US007378257B2

(12) United States Patent
Ulrich et al.

(10) Patent No.: US 7,378,257 B2
(45) Date of Patent: *May 27, 2008

(54) BACTERIAL SUPERANTIGEN VACCINES

(75) Inventors: Robert G. Ulrich, Frederick, MD (US);
Mark A. Olson, Gaithersburg, MD
(US); Sina Bavari, Dillsburg, PA (US)

(73) Assignee: **The United States of America as
represented by the Secretary of the
Army**, Washington, DC (US)

( * ) Notice: Subject to any disclaimer, the term of this
patent is extended or adjusted under 35
U.S.C. 154(b) by 313 days.

This patent is subject to a terminal disclaimer.

(21) Appl. No.: 10/767,687

(22) Filed: Jan. 29, 2004

(65) Prior Publication Data

US 2005/0064526 A1 Mar. 24, 2005

Related U.S. Application Data

(62) Division of application No. 08/882,431, filed on Jun. 25, 1997, now Pat. No. 6,713,284.

(51) Int. Cl.
*C12N 15/09* (2006.01)
(52) U.S. Cl. .................... 435/69.3; 435/69.1; 435/71.1; 435/71.3; 435/320.1; 435/325; 435/252.3; 435/252.33; 536/23.1; 536/23.7
(58) Field of Classification Search ...................... None
See application file for complete search history.

(56) References Cited

FOREIGN PATENT DOCUMENTS

WO   WO 96/36366   11/1996
WO   WO 97/36932   10/1997

OTHER PUBLICATIONS

Briggs et al., "Mutations affecting the superantigen activity of staphylococcal enterotoxin B", Immunology 1997, vol. 90, pp. 169-175.
Rosendahl et al., "A mutation of F47 to A in Staphylococcus enterotoxin A activated the T-cell receptor VB repertoire in vivo", Infection and Immunity, Dec. 1997, vol. 65, No. 12, pp. 5118-5124.
Grossman et al., "Mutation of the disulfide loop in staphylococcal enterotoxin A", J. Immunology, vol. 147, No. 10, pp. 3274-3281, Nov. 15, 1991.
Bavari et al., "Engineered Bacterial Superantigen Vaccines", Vaccines 96, pp. 135-141 (1996).
Bavari et al., "Superantigen Vaccines: A Comparative Study of Genetically Attenuated Receptor-Binding Mutants of Staphylcoccal Enterotoxin A", J. Infectious Diseases, 1996, 174:338-345.
Hurley et al., "Identification of Class II Major Histocompatibility Complex and T Cell Receptor Binding Sites in the Superantigen Toxic Shock Syndrome Toxin 1", J. Exp. Med., vol. 181, 2229-2235, Jun. 1995.

Stiles, et al., "Toxicity of Staphylococcal Enterotoxins Potentiated by Lipopolysaccharide: Major Histocompatibility Complex Class II Molecule Dependency and Cytokine Release", Infection and Immunity, vol. 61, No. 12, pp. 5333-5338, Dec. 1993.
Dannecker et al. (1994) Activation of human T cells by the superantigen Staphylococcus enterotoxin B: Analysis on a cellular level. *Immunobiology* 190: 116-126.
Gonzalo et al. (1992) Expansion and clonal deletion of peripheral T cells induced by bacterial superantigen is independent of the interleukin-2 pathway. *Eur. J. Immunol.* 22:1007-1011.
Bavari et al. (1995) Genetically attenuated bacterial superantigen vaccines. *J. Cellular Biochemistry* Suppl. 21A, abstract C2-204 p. 88.
Bavari et al. (1995) Staphylococcal Enterotoxin A and toxin shock syndrome toxin complete with CD4 for human major histocompatibility complex class II binding. *Infection and Immunity* 63:423-429.
Mahana et al. (1995) A natural mutation of the amino acid residue at position 60 destroys staphylococcal enterotoxin A murine T-cell mitogenicity. *Infection and Immunity* 63:2826-2832.
Woody et al. (1998) Differential immune responses to Staphylococcal enterotoxin B mutations in a hydrophobic loop dominating the interface with major histocompatibility complex class II receptors. *J. Infectious Diseases* 177: 1013-1022.
Bavari, S. et al. (1996) Superantigen vaccines: A comparative study of genetically attenuated receptor-binding mutants of Staphylococcal enterotoxin A. *J. Inf. Dis.* 174:338-345.
Ulrich, R. G. et al. (1995) Staphylococcal enterotoxins A and B share a common structural motif for binding class II major histocompatibility complex molecules. *Nature Structural Biology* 2:554-560.
Stiles, B. G. et al. (1993) Toxicity of Staphylococcal enterotoxins potentiated by lipopolysaccharide: major histocompatibility complex calss II molecule dependency and cytokine release. *Infect. Immun.* 61:5333-5338.
Hurley, J. M. et al. (1995) Identification of class II major histocompatibility complex and T cell receptor binding sites in the superantigen toxin shock syndrome toxin 1. *J. Exp. Med.* 181:2229-2234.
Ulrich, R. G. et al. (1995) Bacterial superantigens in human disease: structure, function and diversity. *Trends in Microbiology* 3: 463-468.
Bavari, S. et al. (1996) Engineered bacterial superantigen vaccines. In *Vaccines 96*, Cold Spring Harbor Laboratory Press, p. 135-141.

*Primary Examiner*—Marianne P Allen
(74) *Attorney, Agent, or Firm*—Elizabeth Arwine

(57) ABSTRACT

The present invention relates to genetically attenuated superantigen toxin vaccines altered such that superantigen attributes are absent, however the superantigen is effectively recognized and an appropriate immune response is produced. The attenuated superantigen toxins are shown to protect animals against challenge with wild type toxin. Methods of producing and using the altered superantigen toxins are described.

13 Claims, 8 Drawing Sheets

Fig. 1

```
                48                   70                    92                        108
SEA   ...SHDQFLQHTILFKGFFTDHSWYNDLLVDFDSKDIVDKYK.GKKVDLYGAYYGYQCA...........GGTPNKTACMYGGVTLHDNNRLTEEKK
SED   ...TGDQFLENTLLYKKFFTDLINFEDLLINFNSKEMAQHFK.SKNVDVYPIRYSINCY...........GGEIDRTACTYGGVTPHEGNKLKERKK
SEE   ...SDDQFLENTLLFKGFFTGHPWYNDLLVDLGSKDATNKYK.GKKVDLYGAYYGYQCA...........GGTPNKTACMYGGVTLHDNNRLTEEKK
SEB   ...SIDQFLYFDLIYSIKDTKLGNYDNVRVEFKNKDLADKYK.DKYVDVFGANYYYQCYFSKKTNDINSHQTDKRKT.CMYGGVTEHNGNQLD..KY
SEC1  ...SVDKFLAHDLIYNISDKKLKNYDKVKTELLNEGLAKKYK.DEVVDVYGSNYYVNCYFSSKDNVGKVTGG...KT.CMYGGITKHEGNHFDNGNL
SEC2  ...SVDKFLAHDLIYNISDKKLKNYDKVKTELLNEDLAKKYK.DEVVDVYGSNYYVNCYFSSKDNVGKVTGG...KT.CMYGGITKHEGNHFDNGNL
SEC3  ...SVDKFLAHDLIYNISDKKLKNYDKVKTELLNEDLAKKYK.DEVVDVYGSNYYVNCYFSSKDNVGKVTGG...KT.CMYGGITKHEGNHFDNGNL
SPEa  ...SVDQLLSHDLIYNVSG...PNYDKLKTELKNQEMATLFK.DKNVDIYGVEYYHLCYLCENAE..........RSACIYGGVTNHEGNHLEIPK.
TSST1 ...VLDNSLGSMRIKNTD......GSISLIIFPSPYYSPAFTKGEKVDLNTKRIKKSQHTSEG..........TYHIF.QISGVTNT EKLPT...P
```

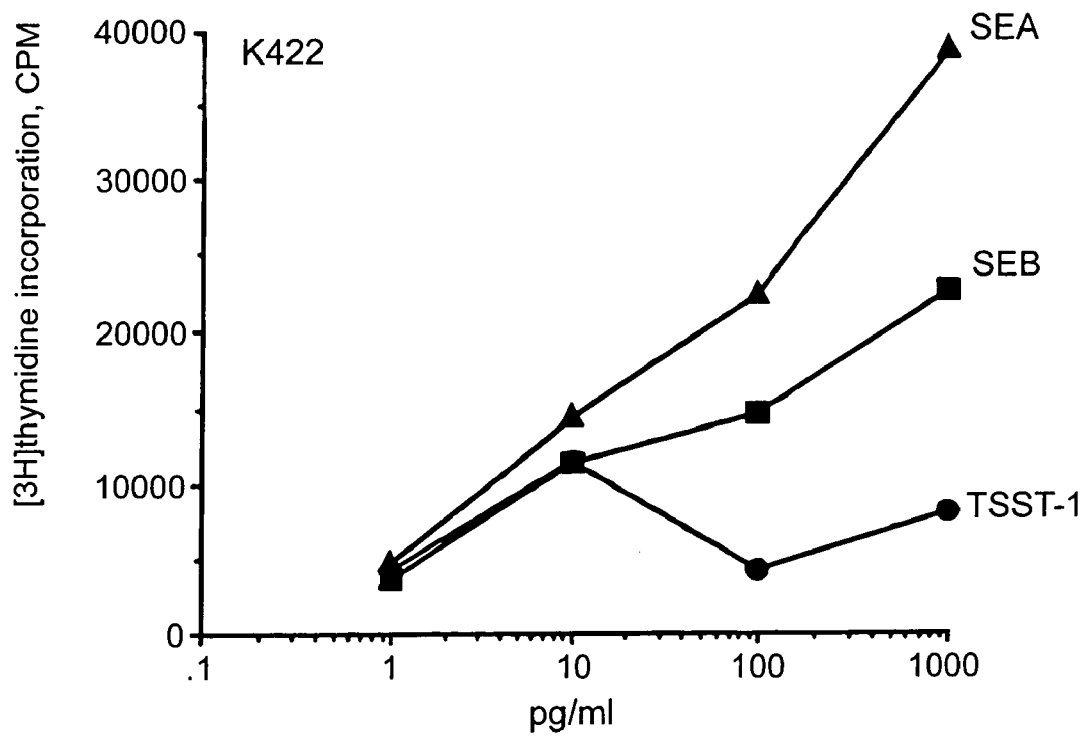
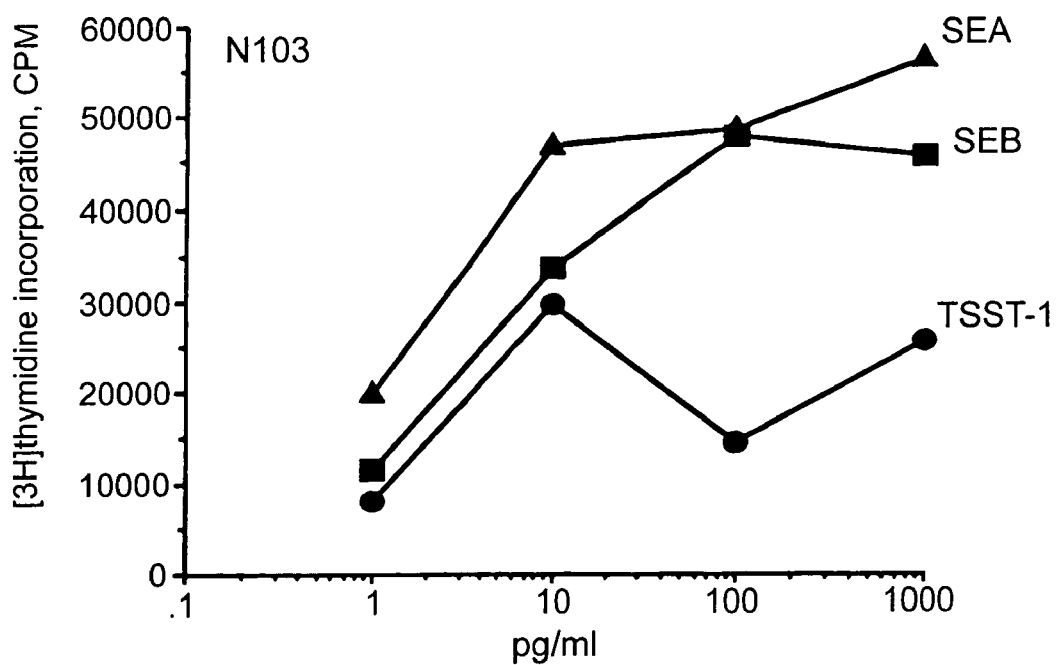
Fig. 6

```
                         SEQUENCE LISTING (1) GENERAL INFORMATION:

(iii) NUMBER OF SEQUENCES: 25

(2) INFORMATION FOR SEQ ID NO: 1:

(i) SEQUENCE CHARACTERISTICS:
           (A) LENGTH: 830
           (B) TYPE: Nucleic Acid
           (C) STRANDEDNESS: Unknown
           (D) TOPOLOGY: Unknown (ii) MOLECULE TYPE: DNA (xi) SEQUENCE DESCRIPTION: SEQ ID NO: 1:

ATGAAAAAAA CAGCATTTAC ATTACTTTTA TTCATTGCCC                         40

TAACGTTGAC AACAAGTCCA CTTGTAAATG GTAGCGAGAA                         80

AAGCGAAGAA ATAAATGAAA AAGATTTGCG AAAAAAGTCT                        120

GAATTGCAGG GAACAGCTTT AGGCAATCTT AAACAAATCT                        160

ATTATTACAA TGAAAAAGCT AAAACTGAAA ATAAAGAGAG                        200

TCACGATCAA TTTCGACAGC ATACTATATT GTTTAAAGGC                        240

TTTTTTACAG ATCATTCGTG GTATAACGAT TTATTAGTAC                        280

GTTTTGATTC AAAGGATATT GTTGATAAAT ATAAAGGGAA                        320

AAAAGTAGAC TTGTATGGTG CTTATGCTGG TTATCAATGT                        360

GCGGGTGGTA CACCAAACAA AACAGCTTGT ATGTATGGTG                        400

GTGTAACGTT ACATGATAAT AATCGATTGA CCGAAGAGAA                        440

AAAAGTGCCG ATCAATTTAT GGCTAGACGG TAAACAAAAT                        480

ACAGTACCTT TGGAAACGGT TAAAACGAAT AAGAAAAATG                        520

TAACTGTTCA GGAGTTGGAT CTTCAAGCAA GACGTTATTT                        560

ACAGGAAAAA TATAATTTAT ATAACTCTGA TGTTTTTGAT                        600

GGGAAGGTTC AGAGGGGATT AATCGTGTTT CATACTTCTA                        640

CAGAACCTTC GGTTAATTAC GATTTATTTG GTGCTCAAGG                        680
```

| | |
|---|---:|
| ACAGTATTCA AATACACTAT TAAGAATATA TAGAGATAAT | 720 |
| AAAACGATTA ACTCTGAAAA CATGCATATT GATATATATT | 760 |
| TATATACAAG TTAAACATGG TAGTTTTGAC CAACGTAATG | 800 |
| TTCAGATTAT TATGAACCGA GAATAATCTA | 830 |

(2) INFORMATION FOR SEQ ID NO: 2:

(i) SEQUENCE CHARACTERISTICS:
        (A) LENGTH: 257
        (B) TYPE: Amino Acid
        (C) STRANDEDNESS: Unknown
        (D) TOPOLOGY: Unknown (ii) MOLECULE TYPE: Peptide (xi) SEQUENCE DESCRIPTION: SEQ ID NO: 2:

```
Met Lys Lys Thr Ala Phe Thr Leu Leu Leu
 1               5                  10

Phe Ile Ala Leu Thr Leu Thr Thr Ser Pro
                15                  20

Leu Val Asn Gly Ser Glu Lys Ser Glu Glu
                25                  30

Ile Asn Glu Lys Asp Leu Arg Lys Lys Ser
                35                  40

Glu Leu Gln Gly Thr Ala Leu Gly Asn Leu
                45                  50

Lys Gln Ile Tyr Tyr Tyr Asn Glu Lys Ala
                55                  60

Lys Thr Glu Asn Lys Glu Ser His Asp Gln
                65                  70

Phe Arg Gln His Thr Ile Leu Phe Lys Gly
                75                  80

Phe Phe Thr Asp His Ser Trp Tyr Asn Asp
                85                  90

Leu Leu Val Arg Phe Asp Ser Lys Asp Ile
                95                 100

Val Asp Lys Tyr Lys Gly Lys Lys Val Asp
               105                 110

Leu Tyr Gly Ala Tyr Ala Gly Tyr Gln Cys
               115                 120

Ala Gly Gly Thr Pro Asn Lys Thr Ala Cys
               125                 130

Met Tyr Gly Gly Val Thr Leu His Asp Asn
               135                 140

Asn Arg Leu Thr Glu Glu Lys Lys Val Pro
               145                 150

Ile Asn Leu Trp Leu Asp Gly Lys Gln Asn
               155                 160

Thr Val Pro Leu Glu Thr Val Lys Thr Asn
               165                 170

Lys Lys Asn Val Thr Val Gln Glu Leu Asp
               175                 180

Leu Gln Ala Arg Arg Tyr Leu Gln Glu Lys
               185                 190
```

```
Tyr Asn Leu Tyr Asn Ser Asp Val Phe Asp
            195                 200

Gly Lys Val Gln Arg Gly Leu Ile Val Phe
            205                 210

His Thr Ser Thr Glu Pro Ser Val Asn Tyr
            215                 220

Asp Leu Phe Gly Ala Gln Gly Gln Tyr Ser
            225                 230

Asn Thr Leu leu Arg Ile Tyr Arg Asp Asn
            235                 240

Lys Thr Ile Asn Ser Glu Asn Met His Ile
            245                 250

Asp Ile Tyr Leu Tyr Thr Ser
            255
```

(2) INFORMATION FOR SEQ ID NO: 3:

(i) SEQUENCE CHARACTERISTICS:
        (A) LENGTH: 757
        (B) TYPE: Nucleic Acid
        (C) STRANDEDNESS: Unknown
        (D) TOPOLOGY: Unknown (ii) MOLECULE TYPE: DNA (xi) SEQUENCE DESCRIPTION: SEQ ID NO: 3:

```
ATGAGAAAAG CGAAGAAATA AATGAAAAAG ATTTGCGAAA                40
AAAGTCTGAA TTGCAGGGAA CAGCTTTAGG CAATCTTAAA                80
CAAATCTATT ATTACAATGA AAAAGCTAAA ACTGAAAATA               120
AAGAGAGTCA CGATCAATTT CGACAGCATA CTATATTGTT               160
TAAAGGCTTT TTTACAGATC ATTCGTGGTA TAACGATTTA               200
TTAGTACGTT TTGATTCAAA GGATATTGTT GATAAATATA               240
AAGGGAAAAA AGTAGACTTG TATGGTGCTT ATGCTGGTTA               280
TCAATGTGCG GGTGGTACAC CAAACAAAAC AGCTTGTATG               320
TATGGTGGTG TAACGTTACA TGATAATAAT CGATTGACCG               360
AAGAGAAAAA AGTGCCGATC AATTTATGGC TAGACGGTAA               400
ACAAAATACA GTACCTTTGG AAACGGTTAA AACGAATAAG               440
AAAAATGTAA CTGTTCAGGA GTTGGATCTT CAAGCAAGAC               480
GTTATTTACA GGAAAAATAT AATTTATATA ACTCTGATGT               520
TTTTGATGGG AAGGTTCAGA GGGGATTAAT CGTGTTTCAT               560
ACTTCTACAG AACCTTCGGT TAATTACGAT TTATTTGGTG               600
CTCAAGGACA GTATTCAAAT ACACTATTAA GAATATATAG               640
AGATAATAAA ACGATTAACT CTGAAAACAT GCATATTGAT               680
ATATATTTAT ATACAAGTTA AACATGGTAG TTTTGACCAA               720
CGTAATGTTC AGATTATTAT GAACCGAGAA TAATCTA                  757
```

(2) INFORMATION FOR SEQ ID NO: 4:

(i) SEQUENCE CHARACTERISTICS:
        (A) LENGTH: 233
        (B) TYPE: Amino Acid
        (C) STRANDEDNESS: Unknown (D) TOPOLOGY: Unknown (ii) MOLECULE TYPE: Peptide (xi) SEQUENCE DESCRIPTION: SEQ ID NO: 4:

Met Glu Lys Ser Glu Ile Asn Glu Lys
              5                  10

Asp Leu Arg Lys Lys Ser Glu Leu Gln Gly
             15                      20

Thr Ala Leu Gly Asn Leu Lys Gln Ile Tyr
             25                      30

Tyr Tyr Asn Glu Lys Ala Lys Thr Glu Asn
             35                      40

Lys Glu Ser His Asp Gln Phe Arg Gln His
             45                      50

Thr Ile Leu Phe Lys Gly Phe Phe Thr Asp
             55                      60

His Ser Trp Tyr Asn Asp Leu Leu Val Arg
             65                      70

Phe Asp Ser Lys Asp Ile Val Asp Lys Tyr
             75                      80

Lys Gly Lys Lys Val Asp Leu Tyr Gly Ala
             85                      90

Tyr Ala Gly Tyr Gln Cys Ala Gly Gly Thr
             95                     100

Pro Asn Lys Thr Ala Cys Met Tyr Gly Gly
            105                     110

Val Thr Leu His Asp Asn Asn Arg Leu Thr
            115                     120

Glu Glu Lys Lys Val Pro Ile Asn Leu Trp
            125                     130

Leu Asp Gly Lys Gln Asn Thr Val Pro Leu
            135                     140

Glu Thr Val Lys Thr Asn Lys Lys Asn Val
            145                     150

Thr Val Gln Glu Leu Asp Leu Gln Ala Arg
            155                     160

Arg Tyr Leu Gln Glu Lys Tyr Asn Leu Tyr
            165                     170

Asn Ser Asp Val Phe Asp Gly Lys Val Gln
            175                     180

Arg Gly Leu Ile Val Phe His Thr Ser Thr
            185                     190

Glu Pro Ser Val Asn Tyr Asp Leu Phe Gly
            195                     200

Ala Gln Gly Gln Tyr Ser Asn Thr Leu Leu
            205                     210

Arg Ile Tyr Arg Asp Asn Lys Thr Ile Asn
            215                     220

Ser Glu Asn Met His Ile Asp Ile Tyr Leu
            225                     230

Tyr Thr Ser (2) INFORMATION FOR SEQ ID NO: 5:

(i) SEQUENCE CHARACTERISTICS:
    (A) LENGTH: 1712
    (B) TYPE: Nucleic Acid
    (C) STRANDEDNESS: Unknown
    (D) TOPOLOGY: Unknown (ii) MOLECULE TYPE: DNA (xi) SEQUENCE DESCRIPTION: SEQ ID NO: 5:

```
GAACTAGGTA GAAAAATAAT TATGAGAAAA CACTATGTTG                40
TTAAAGATGT TTTCGTATAT AAGTTTAGGT GATGTATAGT                80
TACTTAATTT TAAAAGCATA ACTTAATTAA TATAAATAAC               120
ATGAGATTAT TAAATATAAT TAAGTTTCTT TTAATGTTTT               160
TTTAATTGAA TATTTAAGAT TATAACATAT ATTTAAAGTG               200
TATCTAGATA CTTTTTGGGA ATGTTGGATA AAGGAGATAA               240
AAAATGTATA AGAGATTATT TATTTCACAT GTAATTTTGA               280
TATTCGCACT GATATTAGTT ATTTCTACAC CCAACGTTTT               320
AGCAGAGAGT CAACCAGATC CTAAACCAGA TGAGTTGCAC               360
AAATCGAGTA AATTCACTGG TTTGATGGAA GATATGAAAG               400
TTTTGTATGA TGATAATCAT GTATCAGCAA TAAACGTTAA               440
ATCTATAGAT CAATTTCTAT ACTTTGACTT AATATATTCT               480
ATTAAGGACA CTAAGTTAGG GGATTATGAT AATGTTCGAG               520
TCGAATTTAA AAACAAAGAT TTAGCTGATA AATACAAAGA               560
TAAATACGTA GATGTGTTTG GAGCTAATTA TTATTATCAA               600
TGTTATTTTT CTAAAAAAAC GAATGATATT AATTCGCATC               640
AAACTGACAA ACGAAAAACT TGTATGTATG GTGGTGTAAC               680
TGAGCATAAT GGAAACCAAT TAGATAAATA TAGAAGTATT               720
ACTGTTCGGG TATTTGAAGA TGGTAAAAAT TTATTATCTT               760
TTGACGTACA AACTAATAAG AAAAAGGTGA CTGCTCAAGA               800
ATTAGATTAC CTAACTCGTC ACTATTTGGT GAAAAATAAA               840
AAACTCTATG AATTTAACAA CTCGCCTTAT GAAACGGGAT               880
ATATTAAATT TATAGAAAAT GAGAAATAGC TTTTGGTATGA              920
CATGATGCCT GCACCAGGAG ATAAATTTGC CCAATCTAAA               960
TATTTAATGA TGTACAATGA CAATAAAATG GTTGATTCTA              1000
AAGATGTGAA GATTGAAGTT TATCTTACGA CAAAGAAAAA              1040
GTGAAAATTAT ATTTTAGAAA AGTAAATATG AAGAGTTAGT             1080
AATTAAGGCA GGCACTTATA GAGTACCTGC CTTTTCTAAT              1120
ATTATTTAGT TATAGTTATT TTTGTTATAT CTCTCTGATT              1160
TAGCATTAAC CCCTTGTTGC CATTATAGTT TTCACCAACT              1200
TTAGCTGAAA TTGGGGGATC ATTTTTATCT TTACTATGGA              1240
TAGTTACTGT GTCGCCGTTT TTAACGATTT GTTTCTCTTT              1280
TAATTTGTCA GTTAATTTTT TCCATGCATC ATTTGCGTCA              1320
AACCTATTTC CATTTGGATT TATTCTTGAC AAATCAATTC              1360
```

```
TTTTAACACT ATCGGTATTA ATCGGCTTGT TATTAAAATT               1400

ACTAAGTTCA TCTAAATCAG CTGTACCCGT AATACTACTT               1440

TCGCCACCAT TATTTAAATT GTACGTAACA CCAACTGTCT               1480

CATTTGCTGT TTTATCGATA ATATTTGCTT CTTTCAAAGC               1520

ATCTCTTACA TTTTTCCATA AGTCTCTATC TGTTATTTCA               1560

GAAGCCTTTG CAACGTTATT AATACCATTA TAATTTGAAG               1600

AAGAATGAAA ACCTGAACCT ACTGTTGTTA AAACTAAAGC               1640

ACTTGCTATC AATGTTCTTG TTAATAGTTT TTTATTCATT               1680

TTATTTTCTC CTATAACTTA TTTGCAATCG AT                      1712
```

(2) INFORMATION FOR SEQ ID NO: 6:

(i) SEQUENCE CHARACTERISTICS:
        (A) LENGTH: 266
        (B) TYPE: Amino Acid
        (C) STRANDEDNESS: Unknown
        (D) TOPOLOGY: Unknown (ii) MOLECULE TYPE: Peptide (xi) SEQUENCE DESCRIPTION: SEQ ID NO: 6:

```
Met Tyr Lys Arg Leu Phe Ile Ser His Val
                 5                  10

Ile Leu Ile Phe Ala Leu Ile Leu Val Ile
                15                  20

Ser Thr Pro Asn Val Leu Ala Glu Ser Gln
                25                  30

Pro Asp Pro Lys Pro Asp Glu Leu His Lys
                35                  40

Ser Ser Lys Phe Thr Gly Leu Met Glu Asp
                45                  50

Met Lys Val Leu Tyr Asp Asp Asn His Val
                55                  60

Ser Ala Ile Asn Val Lys Ser Ile Asp Gln
                65                  70

Phe Leu Tyr Phe Asp Leu Ile Tyr Ser Ile
                75                  80

Lys Asp Thr Lys Leu Gly Asp Tyr Asp Asn
                85                  90

Val Arg Val Glu Phe Lys Asn Lys Asp Leu
                95                  100

Ala Asp Lys Tyr Lys Asp Lys Tyr Val Asp
               105                  110

Val Phe Gly Ala Asn Tyr Tyr Tyr Gln Cys
               115                  120

Tyr Phe Ser Lys Lys Thr Asn Asp Ile Asn
               125                  130

Ser His Gln Thr Asp Lys Arg Lys Thr Cys
               135                  140

Met Tyr Gly Gly Val Thr Glu His Asn Gly
               145                  150

Asn Gln Leu Asp Lys Tyr Arg Ser Ile Thr
               155                  160
```

```
Val Arg Val Phe Glu Asp Gly Lys Asn Leu
            165                 170

Leu Ser Phe Asp Val Gln Thr Asn Lys Lys
            175                 180

Lys Val Thr Ala Gln Glu Leu Asp Tyr Leu
            185                 190

Thr Arg His Tyr Leu Val Lys Asn Lys Lys
            195                 200

Leu Tyr Glu Phe Asn Asn Ser Pro Tyr Glu
            205                 210

Thr Gly Tyr Ile Lys Phe Ile Glu Asn Glu
            215                 220

Asn Ser Phe Trp Tyr Asp Met Met Pro Ala
            225                 230

Pro Gly Asp Lys Phe Ala Gln Ser Lys Tyr
            235                 240

Leu Met Met Tyr Asn Asp Asn Lys Met Val
            245                 250

Asp Ser Lys Asp Val Lys Ile Glu Val Tyr
            255                 260

Leu Thr Thr Lys Lys Lys
            265
```

(2) INFORMATION FOR SEQ ID NO: 7:

(i) SEQUENCE CHARACTERISTICS:
        (A) LENGTH: 1712
        (B) TYPE: Nucleic Acid
        (C) STRANDEDNESS: Unknown
        (D) TOPOLOGY: Unknown (ii) MOLECULE TYPE: DNA (xi) SEQUENCE DESCRIPTION: SEQ ID NO: 7:

```
GAACTAGGTA GAAAAATAAT TATGAGAAAA CACTATGTTG                      40

TTAAAGATGT TTTCGTATAT AAGTTTAGGT GATGTATAGT                      80

TACTTAATTT TAAAAGCATA ACTTAATTAA TATAAATAAC                     120

ATGAGATTAT TAAATATAAT TAAGTTTCTT TTAATGTTTT                     160

TTTAATTGAA TATTTAAGAT TATAACATAT ATTTAAAGTG                     200

TATCTAGATA CTTTTTGGGA ATGTTGGATA AAGGAGATAA                     240

AAAATGTATA AGAGATTATT TATTTCACAT GTAATTTTGA                     280

TATTCGCACT GATATTAGTT ATTTCTACAC CCAACGTTTT                     320

AGCAGAGAGT CAACCAGATC CTAAACCAGA TGAGTTGCAC                     360

AAATCGAGTA AATTCACTGG TTTGATGGAA ATATGAAAG                      400

TTTTGTATGA TGATAATCAT GTATCAGCAA TAAACGTTAA                     440

ATCTATAGAT CAATTTCGAT ACTTTGACTT AATATATTCT                     480

ATTAAGGACA CTAAGTTAGG GAATTATGAT AATGTTCGAG                     520

TCGAATTTAA AAACAAAGAT TTAGCTGATA AATACAAAGA                     560

TAAATACGTA GATGTGTTTG GAGCTAATGC TTATTATCAA                     600

TGTGCTTTTT CTAAAAAAAC GAATGATATT AATTCGCATC                     640

AAACTGACAA ACGAAAAACT TGTATGTATG GTGGTGTAAC                     680
```

```
TGAGCATAAT GGAAACCAAT TAGATAAATA TAGAAGTATT         720

ACTGTTCGGG TATTTGAAGA TGGTAAAAAT TTATTATCTT         760

TTGACGTACA AACTAATAAG AAAAAGGTGA CTGCTCAAGA         800

ATTAGATTAC CTAACTCGTC ACTATTTGGT GAAAAATAAA         840

AAACTCTATG AATTTAACAA CTCGCCTTAT GAAACGGGAT         880

ATATTAAATT TATAGAAAAT GAGAATAGCT TTTGGTATGA         920

CATGATGCCT GCACCAGGAG ATAAATTTGA CCAATCTAAA         960

TATTTAATGA TGTACAATGA CAATAAAATG GTTGATTCTA        1000

AAGATGTGAA GATTGAAGTT TATCTTACGA CAAAGAAAAA        1040

GTGAAATTAT ATTTTAGAAA AGTAAATATG AAGAGTTAGT        1080

AATTAAGGCA GGCACTTATA GAGTACCTGC CTTTTCTAAT        1120

ATTATTTAGT TATAGTTATT TTTGTTATAT CTCTCTGATT        1160

TAGCATTAAC CCCTTGTTGC CATTATAGTT TTCACCAACT        1200

TTAGCTGAAA TTGGGGGATC ATTTTTATCT TTACTATGGA        1240

TAGTTACTGT GTCGCCGTTT TTAACGATTT GTTTCTCTTT        1280

TAATTTGTCA GTTAATTTTT TCCATGCATC ATTTGCGTCA        1320

AACCTATTTC CATTTGGATT TATTCTTGAC AAATCAATTC        1360

TTTTAACACT ATCGGTATTA ATCGGCTTGT TATTAAAATT        1400

ACTAAGTTCA TCTAAATCAG CTGTACCCGT AATACTACTT        1440

TCGCCACCAT TATTTAAATT GTACGTAACA CCAACTGTCT        1480

CATTTGCTGT TTTATCGATA ATATTTGCTT CTTTCAAAGC        1520

ATCTCTTACA TTTTTCCATA AGTCTCTATC TGTTATTTCA        1560

GAAGCCTTTG CAACGTTATT AATACCATTA TAATTTGAAG        1600

AAGAATGAAA ACCTGAACCT ACTGTTGTTA AAACTAAAGC        1640

ACTTGCTATC AATGTTCTTG TTAATAGTTT TTTATTCATT        1680

TTATTTTCTC CTATAACTTA TTTGCAATCG AT               1712

(2) INFORMATION FOR SEQ ID NO: 8:

(i) SEQUENCE CHARACTERISTICS:
         (A) LENGTH: 266
         (B) TYPE: Amino Acid
         (C) STRANDEDNESS: Unknown
         (D) TOPOLOGY: Unknown (ii) MOLECULE TYPE: Peptide (xi) SEQUENCE DESCRIPTION: SEQ ID NO: 8:

Met Tyr Lys Arg Leu Phe Ile Ser His Val
                  5                  10

Ile Leu Ile Phe Ala Leu Ile Leu Val Ile
                 15                  20

Ser Thr Pro Asn Val Leu Ala Glu Ser Gln
                 25                  30

Pro Asp Pro Lys Pro Asp Glu Leu His Lys
                 35                  40

Ser Ser Lys Phe Thr Gly Leu Met Glu Asn
```

```
                        45                  50
Met Lys Val Leu Tyr Asp Asp Asn His Val
                    55                  60

Ser Ala Ile Asn Val Lys Ser Ile Asp Gln
                    65                  70

Phe Arg Tyr Phe Asp Leu Ile Tyr Ser Ile
                    75                  80

Lys Asp Thr Lys Leu Gly Asn Tyr Asp Asn
                    85                  90

Val Arg Val Glu Phe Lys Asn Lys Asp Leu
                    95                 100

Ala Asp Lys Tyr Lys Asp Lys Tyr Val Asp
                   105                 110

Val Phe Gly Ala Asn Ala Tyr Tyr Gln Cys
                   115                 120

Ala Phe Ser Lys Lys Thr Asn Asp Ile Asn
                   125                 130

Ser His Gln Thr Asp Lys Arg Lys Thr Cys
                   135                 140

Met Tyr Gly Gly Val Thr Glu His Asn Gly
                   145                 150

Asn Gln Leu Asp Lys Tyr Arg Ser Ile Thr
                   155                 160

Val Arg Val Phe Glu Asp Gly Lys Asn Leu
                   165                 170

Leu Ser Phe Asp Val Gln Tyr Asn Lys Lys
                   175                 180

Lys Val Thr Ala Gln Glu Leu Asp Tyr Leu
                   185                 190

Thr Arg His Tyr Leu Val Lys Asn Lys Lys
                   195                 200

Leu Tyr Glu Phe Asn Asn Ser Pro Tyr Glu
                   205                 210

Thr Gly Tyr Ile Lys Phe Ile Glu Asn Glu
                   215                 220

Asn Ser Phe Trp Tyr Asp Met Met Pro Ala
                   225                 230

Pro Gly Asp Lys Phe Asp Gln Ser Lys Tyr
                   235                 240

Leu Met Met Tyr Asn Asp Asn Lys Met Val
                   245                 250

Asp Ser Lys Asp Val Lys Ile Glu Val Tyr
                   255                 260

Leu Thr Thr Lys Lys Lys
                   265

(2) INFORMATION FOR SEQ ID NO: 9:

(i) SEQUENCE CHARACTERISTICS:
        (A) LENGTH: 1388
        (B) TYPE: Nucleic Acid
        (C) STRANDEDNESS: Unknown
        (D) TOPOLOGY: Unknown (ii) MOLECULE TYPE: DNA
```

(xi) SEQUENCE DESCRIPTION: SEQ ID NO: 9:

| | |
|---|---|
| ATGAGTCAAC CAGATCCTAA ACCAGATGAG TTGCACAAAT | 40 |
| CGAGTAAATT CACTGGTTTG ATGGAAAATA TGAAAGTTTT | 80 |
| GTATGATGAT AATCATGTAT CAGCAATAAA CGTTAAATCT | 120 |
| ATAGATCAAT TTCGATACTT TGACTTAATA TATTCTATTA | 160 |
| AGGACACTAA GTTAGGGAAT TATGATAATG TTCGAGTCGA | 200 |
| ATTTAAAAAC AAAGATTTAG CTGATAAATA CAAAGATAAA | 240 |
| TACGTAGATG TGTTTGGAGC TAATGCTTAT TATCAATGTG | 280 |
| CTTTTTCTAA AAAAACGAAT GATATTAATT CGCATCAAAC | 320 |
| TGACAAACGA AAAACTTGTA TGTATGGTGG TGTAACTGAG | 360 |
| CATAATGGAA ACCAATTAGA TAAATATAGA AGTATTACTG | 400 |
| TTCGGGTATT TGAAGATGGT AAAAATTTAT TATCTTTTGA | 440 |
| CGTACAAACT AATAAGAAAA AGGTGACTGC TCAAGAATTA | 480 |
| GATTACCTAA CTCGTCACTA TTTGGTGAAA AATAAAAAAC | 520 |
| TCTATGAATT TAACAACTCG CCTTATGAAA CGGGATATAT | 560 |
| TAAATTTATA GAAAATGAGA ATAGCTTTTG GTATGACATG | 600 |
| ATGCCTGCAC CAGGAGATAA ATTTGACCAA TCTAAATATT | 640 |
| TAATGATGTA CAATGACAAT AAAATGGTTG ATTCTAAAGA | 680 |
| TGTGAAGATT GAAGTTTATC TTACGACAAA GAAAAAGTGA | 720 |
| AATTATATTT TAGAAAAGTA AATATGAAGA GTTAGTAATT | 760 |
| AAGGCAGGCA CTTATAGAGT ACCTGCCTTT TCTAATATTA | 800 |
| TTTAGTTATA GTTATTTTTG TTATATCTCT CTGATTTAGC | 840 |
| ATTAACCCCT TGTTGCCATT ATAGTTTTCAC CAACTTTAG | 880 |
| CTGAAATTGG GGGATCATTT TTATCTTTAC TATGGATAGT | 920 |
| TACTGTGTCG CCGTTTTTAA CGATTTGTTT CTCTTTTAAT | 960 |
| TTGTCAGTTA ATTTTTTCCA TGCATCATTT GCGTCAAACC | 1000 |
| TATTTCCATT TGGATTTATT CTTGACAAAT CAATTCTTTT | 1040 |
| AACACTATCG GTATTAATCG GCTTGTTATT AAAATTACTA | 1080 |
| AGTTCATCTA AATCAGCTGT ACCCGTAATA CTACTTTCGC | 1120 |
| CACCATTATT TAAATTGTAC GTAACACCAA CTGTCTCATT | 1160 |
| TGCTGTTTTA TCGATAATAT TTGCTTCTTT CAAAGCATCT | 1200 |
| CTTACATTTT TCCATAAGTC TCTATCTGTT ATTTCAGAAG | 1240 |
| CCTTTGCAAC GTTATTAATA CCATTATAAT TTGAAGAAGA | 1280 |
| ATGAAAACCT GAACCTACTG TTGTTAAAAC TAAAGCACTT | 1320 |
| GCTATCAATG TTCTTGTTAA TAGTTTTTTA TTCATTTTAT | 1360 |
| TTTCTCCTAT AACTTATTTG CAATCGAT | 1388 |

(2) INFORMATION FOR SEQ ID NO: 10:

(i) SEQUENCE CHARACTERISTICS:
        (A) LENGTH: 239
        (B) TYPE: Amino Acid
        (C) STRANDEDNESS: Unknown (D) TOPOLOGY: Unknown (ii) MOLECULE TYPE: Peptide (xi) SEQUENCE DESCRIPTION: SEQ ID NO: 10:

```
Met Ser Gln Pro Asp Pro Lys Pro Asp Glu
                  5                  10

Leu His Lys Ser Ser Lys Phe Thr Gly Leu
                 15                  20

Met Glu Asn Met Lys Val Leu Tyr Asp Asp
                 25                  30

Asn His Val Ser Ala Ile Asn Val Lys Ser
                 35                  40

Ile Asp Gln Phe Arg Tyr Phe Asp Leu Ile
                 45                  50

Tyr Ser Ile Lys Asp Thr Lys Leu Gly Asn
                 55                  60

Tyr Asp Asn Val Arg Val Glu Phe Lys Asn
                 65                  70

Lys Asp Leu Ala Asp Lys Tyr Lys Asp Lys
                 75                  80

Tyr Val Asp Val Phe Gly Ala Asn Ala Tyr
                 85                  90

Tyr Gln Cys Ala Phe Ser Lys Lys Thr Asn
                 95                 100

Asp Ile Asn Ser His Gln Thr Asp Lys Arg
                105                 110

Lys Thr Cys Met Tyr Gly Gly Val Thr Glu
                115                 120

His Asn Gly Asn Gln Leu Asp Lys Tyr Arg
                125                 130

Ser Ile Thr Val Arg Val Phe Glu Asp Gly
                135                 140

Lys Asn Leu Leu Ser Phe Asp Val Gln Thr
                145                 150

Asn Lys Lys Lys Val Thr Ala Gln Glu Leu
                155                 160

Asp Tyr Leu Thr Arg His Tyr Leu Val Lys
                165                 170

Asn Lys Lys Leu Tyr Glu Phe Asn Asn Ser
                175                 180

Pro Tyr Glu Thr Gly Tyr Ile Lys Phe Ile
                185                 190

Glu Asn Glu Asn Ser Phe Trp Tyr Asp Met
                195                 200

Met Pro Ala Pro Gly Asp Lys Phe Asp Gln
                205                 210

Ser Lys Tyr Leu Met Met Tyr Asn Asp Asn
                215                 220

Lys Met Val Asp Ser Lys Asp Val Lys Ile
                225                 230

Glu Val Tyr Leu Thr Thr Lys Lys Lys
                235
```

```
(2) INFORMATION FOR SEQ ID NO: 11:

(i) SEQUENCE CHARACTERISTICS:
        (A) LENGTH: 731
        (B) TYPE: Nucleic Acid
        (C) STRANDEDNESS: Unknown
        (D) TOPOLOGY: Unknown (ii) MOLECULE TYPE: DNA (xi) SEQUENCE DESCRIPTION: SEQ ID NO: 11:

TAAGGAGAAT TAAAAATGAA TAAAAAATTA CTAATGAATT                    40

TTTTTATCGT AAGCCCTTTG TTGCTTGCGA CAACTGCTAC                    80

AGATTTTACC CCTGTTCCCT TATCATCTAA TCAAATAATC                   120

AAAACTGCAA AAGCATCTAC AAACGATAAT ATAAAGGATT                   160

TGCTAGACTG GTATAGTAGT GGGTCTGACA CTTTTACAAA                   200

TAGTGAAGTT TTAGATAATT CCAGAGGATC TATGCGTATA                   240

AAAAACACAG ATGGCAGCAT CAGCTTGATA ATTTTTCCGA                   280

GTCCTTATTA TAGCCCTGCT TTTACAAAAG GGGAAAAAGT                   320

TGACTTAAAC ACAAAAAGAA CTAAAAAAAG CCAACATACT                   360

AGCGAAGGAA CTTATATCCA TTTCCAAATA AGTGGCGTTA                   400

CAAATACTGA AAAATTACCT ACTCCAATAG AACTACCTTT                   440

AAAAGTTAAG GTTCATGGTA AAGATAGCCC CTTAAAGTAT                   480

GGGCCAAAGT TCGATAAAAA ACAATTAGCT ATATCAACTT                   520

TAGACTTTGA AATTCGTCAT CAGCTAACTC AAATACATGG                   560

ATTATATCGT TCAAGCGATA AAACGGGTGG TTATTGGAAA                   600

ATAACAATGA ATGACGGATC CACATATCAA AGTGATTTAT                   640

CTAAAAAGTT TGAATACAAT ACTGAAAAAC CACCTATAAA                   680

TATTGATGAA ATAAAAACTA TAGAAGCAGA AATTAATTAA                   720

TTTACCACTT T                                                  731

(2) INFORMATION FOR SEQ ID NO: 12:

(i) SEQUENCE CHARACTERISTICS:
        (A) LENGTH: 234
        (B) TYPE: Amino Acid
        (C) STRANDEDNESS: Unknown
        (D) TOPOLOGY: Unknown (ii) MOLECULE TYPE: Peptide (xi) SEQUENCE DESCRIPTION: SEQ ID NO: 12:

Met Asn Lys Lys Leu Leu Met Asn Phe Phe
                  5                  10

Ile Val Ser Pro Leu Leu Leu Ala Thr Thr
                 15                  20

Ala Thr Asp Phe Thr Pro Val Pro Leu Ser
                 25                  30

Ser Asn Gln Ile Ile Lys Thr Ala Lys Ala
                 35                  40

Ser Thr Asn Asp Asn Ile Lys Asp Leu Leu
                 45                  50

Asp Trp Tyr Ser Ser Gly Ser Asp Thr Phe
```

```
                    55                  60
Thr Asn Ser Glu Val Leu Asp Asn Ser Arg
                    65                  70
Gly Ser Met Arg Ile Lys Asn Thr Asp Gly
                    75                  80
Ser Ile Ser Leu Ile Ile Phe Pro Ser Pro
                    85                  90
Tyr Tyr Ser Pro Ala Phe Thr Lys Gly Glu
                    95                 100
Lys Val Asp Leu Asn Thr Lys Arg Thr Lys
                   105                 110
Lys Ser Gln His Thr Ser Glu Gly Thr Tyr
                   115                 120
Ile His Phe Gln Ile Ser Gly Val Thr Asn
                   125                 130
Thr Glu Lys Leu Pro Thr Pro Ile Glu Leu
                   135                 140
Pro Leu Lys Val Lys Val His Gly Lys Asp
                   145                 150
Ser Pro Leu Lys Tyr Gly Pro Lys Phe Asp
                   155                 160
Lys Lys Gln Leu Ala Ile Ser Thr Leu Asp
                   165                 170
Phe Glu Ile Arg His Gln Leu Thr Gln Ile
                   175                 180
His Gly Leu Tyr Arg Ser Ser Asp Lys Thr
                   185                 190
Gly Gly Tyr Trp Lys Ile Thr Met Asn Asp
                   195                 200
Gly Ser Thr Tyr Gln Ser Asp Leu Ser Lys
                   205                 210
Lys Phe Glu Tyr Asn Thr Glu Lys Pro Pro
                   215                 220
Ile Asn Ile Asp Glu Ile Lys Thr Ile Glu
                   225                 230
Ala Glu Ile Asn (2) INFORMATION FOR SEQ ID NO: 13:

(i) SEQUENCE CHARACTERISTICS:
        (A) LENGTH: 1095
        (B) TYPE: Nucleic Acid
        (C) STRANDEDNESS: Unknown
        (D) TOPOLOGY: Unknown (ii) MOLECULE TYPE: DNA (xi) SEQUENCE DESCRIPTION: SEQ ID NO: 13:

ATCATTAAAT ATAATTAATT TTCTTTTAAT ATTTTTTTAA                          40

TTGAATATTT AAGATTATAA GATATATTTA AAGTGTATCT                          80

AGATACTTTT TGGGAATGTT GGATGAAGGA GATAAAAATG                         120

AATAAGAGTC GATTTATTTC ATGCGTAATT TTGATATTCG                         160

CACTTATACT AGTTCTTTTT ACACCCAACG TATTAGCAGA                         200

GAGCCAACCA GACCCTACGC CAGATGAGTT GCACAAAGCG                         240
```

```
AGTAAATTCA CTGGTTTGAT GGAAAATATG AAAGTTTTAT           280

ATGATGATCA TTATGTATCA GCAACTAAAG TTAAGTCTGT           320

AGATAAATTT AGGGCACATG ATTTAATTTA TAACATTAGT           360

GATAAAAAAC TGAAAAATTA TGACAAAGTG AAAACAGAGT           400

TATTAAATGA AGGTTTAGCA AAGAAGTACA AAGATGAAGT           440

AGTTGATGTG TATGGATCAA ATTACTATGT AAACTGCTAT           480

TTTTCATCCA AAGATAATGT AGGTAAAGTT ACAGGTGGCA           520

AAACTTGTAT GTATGGAGGA ATAACAAAAC ATGAAGGAAA           560

CCACTTTGAT AATGGGAACT TACAAAATGT ACTTATAAGA           600

GTTTATGAAA ATAAAAGAAA CACAATTTCT TTTGAAGTGC           640

AAACTGATAA GAAAGTGTA ACAGCTCAAG AACTAGACAT            680

AAAAGCTAGG AATTTTTTAA TTAATAAAAA AAATTTGTAT           720

GAGTTTAACA GTTCACCATA TGAAACAGGA TATATAAAAT           760

TTATTGAAAA TAACGGCAAT ACTTTTTGGT ATGATATGAT           800

GCCTGCACCA GGCGATAAGT TTGACCAATC TAAATATTTA           840

ATGATGTACA ACGACAATAA AACGGTTGAT TCTAAAAGTG           880

TGAAGATAGA AGTCCACCTT ACAACAAAGA ATGGATAATG           920

TTAATCCGAT TTTGATATAA AAAGTGAAAG TATTAGATAT           960

ATTTGAAAGG TAAGTACTTC GGTGCTTGCC TTTTTAGGAT          1000

GCATATATAT AGATTAAACC GCACTTCTAT ATTAATAGAA          1040

AGTGCGGTTA TTTATACACT CAATCTAAAC TATAATAATT          1080

GGAATCATCT TCAAA                                    1095

(2) INFORMATION FOR SEQ ID NO: 14:

(i) SEQUENCE CHARACTERISTICS:
        (A) LENGTH: 266
        (B) TYPE: Amino Acid
        (C) STRANDEDNESS: Unknown
        (D) TOPOLOGY: Unknown (ii) MOLECULE TYPE: Peptide (xi) SEQUENCE DESCRIPTION: SEQ ID NO: 14:

Met Asn Lys Ser Arg Phe Ile Ser Cys Val
                 5                   10

Ile Leu Ile Phe Ala Leu Ile Leu Val Leu
                15                   20

Phe Thr Pro Asn Val Leu Ala Glu Ser Gln
                25                   30

Pro Asp Pro Thr Pro Asp Glu Leu His Lys
                35                   40

Ala Ser Lys Phe Thr Gly Leu Met Glu Asn
                45                   50

Met Lys Val Leu Tyr Asp Asp His Tyr Val
                55                   60

Ser Ala Thr Lys Val Lys Ser Val Asp Lys
                65                   70
```

```
Phe Arg Ala His Asp Leu Ile Tyr Asn Ile
             75                  80

Ser Asp Lys Lys Leu Lys Asn Tyr Asp Lys
             85                  90

Val Lys Thr Glu Leu Leu Asn Glu Gly Leu
             95                 100

Ala Lys Lys Tyr Lys Asp Glu Val Val Asp
            105                 110

Val Tyr Gly Ser Asn Tyr Tyr Val Asn Cys
            115                 120

Tyr Phe Ser Ser Lys Asp Asn Val Gly Lys
            125                 130

Val Thr Gly Gly Lys Thr Cys Met Tyr Gly
            135                 140

Gly Ile Thr Lys His Glu Gly Asn His Phe
            145                 150

Asp Asn Gly Asn Leu Gln Asn Val Leu Ile
            155                 160

Arg Val Tyr Glu Asn Lys Arg Asn Thr Ile
            165                 170

Ser Phe Glu Val Gln Thr Asp Lys Lys Ser
            175                 180

Val Thr Ala Gln Glu Leu Asp Ile Lys Ala
            185                 190

Arg Asn Phe Leu Ile Asn Lys Lys Asn Leu
            195                 200

Tyr Glu Phe Asn Ser Ser Phe Tyr Glu Thr
            205                 210

Gly Tyr Ile Lys Phe Ile Glu Asn Asn Gly
            215                 220

Asn Thr Phe Trp Tyr Asp Met Met Pro Ala
            225                 230

Pro Gly Asp Lys Phe Asp Gln Ser Lys Tyr
            235                 240

Leu Met Met Tyr Asn Asp Asn Lys Thr Val
            245                 250

Asp Ser Lys Ser Val Lys Ile Glu Val His
            255                 260

Leu Thr Thr Lys Asn Gly
            265

(2) INFORMATION FOR SEQ ID NO: 15:

(i) SEQUENCE CHARACTERISTICS:
        (A) LENGTH: 1837
        (B) TYPE: Nucleic Acid
        (C) STRANDEDNESS: Unknown
        (D) TOPOLOGY: Unknown (ii) MOLECULE TYPE: DNA (xi) SEQUENCE DESCRIPTION: SEQ ID NO: 15:

TCATGTTTGA CAGCTTATCA TCGATAAGCT TACTTTTCGA                 40

ATCAGGTCTA TCCTTGAAAC AGGTGCAACA TAGATTAGGG                 80

CATGGAGATT TACCAGACAA CTATGAACGT ATATACTCAC                120
```

```
ATCACGCAAT CGGCAATTGA TGACATTGGA ACTAAATTCA          160

ATCAATTTGT TACTAACAAG CAACTAGATT GACAACTAAT          200

TCTCAACAAA CGTTAATTTA ACAACATTCA AGTAACTCCC          240

ACCAGCTCCA TCAATGCTTA CCGTAAGTAA TCATAACTTA          280

CTAAAACCTT GTTACATCAA GGTTTTTTCT TTTTGTCTTG          320

TTCATGAGTT ACCATAACTT TCTATATTAT TGACAACTAA          360

ATTGACAACT CTTCAATTAT TTTTCTGTCT ACTCAAAGTT          400

TTCTTCATTT GATATAGTCT AATTCCACCA TCACTTCTTC          440

CACTCTCTCT ACCGTCACAA CTTCATCATC TCTCACTTTT          480

TCGTGTGGTA ACACATAATC AAATATCTTT CCGTTTTTAC          520

GCACTATCGC TACTGTGTCA CCTAAAATAT ACCCCTTATC          560

AATCGCTTCT TTAAACTCAT CTATATATAA CATATTTCAT          600

CCTCCTACCT ATCTATTCGT AAAAGATAA AAATAACTAT           640

TGTTTTTTTT GTTATTTTAT AATAAAATTA TTAATATAAG          680

TTAATGTTTT TTAAAAATAT ACAATTTTAT TCTATTTATA          720

GTTAGCTATT TTTCATTGT TAGTAATATT GGTGAATTGT           760

AATAACCTTT TTAAATCTAG AGGAGAACCC AGATATAAAA          800

TGGAGGAATA TTAATGGAAA ACAATAAAAA AGTATTGAAG          840

AAAATGGTAT TTTTGTTTT AGTGACATTT CTTGGACTAA           880

CAATCTCGCA AGAGGTATTT GCTCAACAAG ACCCCGATCC          920

AAGCCAACTT CACAGATCTA GTTAGTTAA AAACCTTCAA           960

AATATATATT TTCTTTATGA GGGTGACCCT GTTACTCACG          1000

AGAATGTGAA ATCTGTTGAT CAACTTAGAT CTCACGATTT          1040

AATATATAAT GTTTCAGGGC CAAATTATGA TAAATTAAAA          1080

ACTGAACTTA AGAACCAAGA GATGGCAACT TTATTTAAGG          1120

ATAAAAACGT TGATATTTAT GGTGTAGAAT ATTACCATCT          1160

CTGTTATTTA TGTGAAAATG CAGAAAGGAG TGCATGTATC          1200

TACGGAGGGG TAACAAATCA TGAAGGGAAT CATTTAGAAA          1240

TTCCTAAAAA GATAGTCGTT AAAGTATCAA TCGATGGTAT          1280

CCAAAGCCTA TCATTTGATA TTGAAACAAA TAAAAAAATG          1320

GTAACTGCTC AAGAATTAGA CTATAAAGTT AGAAAATATC          1360

TTACAGATAA TAAGCAACTA TATACTAATG GACCTTCTAA          1400

ATATGAAACT GGATATATAA AGTTCATACC TAAGAATAAA          1440

GAAAGTTTTT GGTTTGATTT TTTCCCTGAA CCAGAATTTA          1480

CTCAATCTAA ATATCTTATG ATATATAAAG ATAATGAAAC          1520

GCTTGACTCA AACACAAGCC AAATTGAAGT CTACCTAACA          1560

ACCAAGTAAC TTTTTGCTTT TGGCAACCTT ACCTACTGCT          1600

GGATTTAGAA ATTTTATTGC AATTCTTTTA TTAATGTAAA          1640

AACCGCTCAT TTGATGAGCG GTTTTGTCTT ATCTAAAGGA          1680

GCTTTACCTC CTAATGCTGC AAAATTTTAA ATGTTGGATT          1720
```

-continued

```
TTTGTATTTG TCTATTGTAT TTGATGGGTA ATCCCATTTT                    1760

TCGACAGACA TCGTCGTGCC ACCTCTAACA CCAAAATCAT                    1800

AGACAGGAGC TTGTAGCTTA GCAACTATTT TATCGTC                       1837
```

(2) INFORMATION FOR SEQ ID NO: 16:

(i) SEQUENCE CHARACTERISTICS:
        (A) LENGTH: 251
        (B) TYPE: Amino Acid
        (C) STRANDEDNESS: Unknown
        (D) TOPOLOGY: Unknown (ii) MOLECULE TYPE: Peptide (xi) SEQUENCE DESCRIPTION: SEQ ID NO: 16:

```
Met Glu Asn Asn Lys Lys Val Leu Lys Lys
                 5                  10

Met Val Phe Phe Val Leu Val Thr Phe Leu
                15                  20

Gly Leu Thr Ile Ser Gln Glu Val Phe Ala
                25                  30

Gln Gln Asp Pro Asp Pro Ser Gln Leu His
                35                  40

Arg Ser Ser Leu Val Lys Asn Leu Gln Asn
                45                  50

Ile Tyr Phe Leu Tyr Glu Gly Asp Pro Val
                55                  60

Thr His Glu Asn Val Lys Ser Val Asp Gln
                65                  70

Leu Arg Ser His Asp Leu Ile Tyr Asn Val
                75                  80

Ser Gly Pro Asn Tyr Asp Lys Leu Lys Thr
                85                  90

Glu Leu Lys Asn Gln Glu Met Ala Thr Leu
                95                 100

Phe Lys Asp Lys Asn Val Asp Ile Tyr Gly
               105                 110

Val Glu Tyr Tyr His Leu Cys Tyr Leu Cys
               115                 120

Glu Asn Ala Glu Arg Ser Ala Cys Ile Tyr
               125                 130

Gly Gly Val Thr Asn His Glu Gly Asn His
               135                 140

Leu Glu Ile Pro Lys Lys Ile Val Val Lys
               145                 150

Val Ser Ile Asp Gly Ile Gln Ser Leu Ser
               155                 160

Phe Asp Ile Glu Thr Asn Lys Lys Met Val
               165                 170

Thr Ala Gln Glu Leu Asp Tyr Lys Val Arg
               175                 180

Lys Tyr Leu Thr Asp Asn Lys Gln Leu Tyr
               185                 190

Thr Asn Gly Pro Ser Lys Tyr Glu Thr Gly
               195                 200
```

```
Tyr Ile Lys Phe Ile Pro Lys Asn Lys Glu
            205                 210

Ser Phe Trp Phe Asp Phe Phe Pro Glu Pro
            215                 220

Glu Phe Thr Gln Ser Lys Tyr Leu Met Ile
            225                 230

Tyr Lys Asp Asn Glu Thr Leu Asp Ser Asn
            235                 240

Thr Ser Gln Ile Glu Val Tyr Leu Thr Thr
            245                 250

Lys (2) INFORMATION FOR SEQ ID NO: 17:

(i) SEQUENCE CHARACTERISTICS:
        (A) LENGTH: 82
        (B) TYPE: Amino Acid
        (C) STRANDEDNESS: Unknown
        (D) TOPOLOGY: Unknown (ii) MOLECULE TYPE: Peptide (xi) SEQUENCE DESCRIPTION: SEQ ID NO: 17:

Ser His Asp Gln Phe Leu Gln His Thr Ile
            5                   10

Leu Phe Lys Gly Phe Phe Thr Asp His Ser
            15                  20

Trp Tyr Asn Asp Leu Leu Val Asp Phe Asp
            25                  30

Ser Lys Asp Ile Val Asp Lys Tyr Lys Gly
            35                  40

Lys Lys Val Asp Leu Tyr Gly Ala Tyr Tyr
            45                  50

Gly Tyr Gln Cys Ala Gly Gly Thr Pro Asn
            55                  60

Lys Thr Ala Cys Met Tyr Gly Gly Val Thr
            65                  70

Leu His Asp Asn Asn Arg Leu Thr Glu Glu
            75                  80

Lys Lys (2) INFORMATION FOR SEQ ID NO: 18:

(i) SEQUENCE CHARACTERISTICS:
        (A) LENGTH: 82
        (B) TYPE: Amino Acid
        (C) STRANDEDNESS: Unknown
        (D) TOPOLOGY: Unknown (ii) MOLECULE TYPE: Peptide (xi) SEQUENCE DESCRIPTION: SEQ ID NO: 18:

Thr Gly Asp Gln Phe Leu Glu Asn Thr Leu
            5                   10

Leu Tyr Lys Lys Phe Phe Thr Asp Leu Ile
            15                  20

Asn Phe Glu Asp Leu Leu Ile Asn Phe Asn
            25                  30
```

```
Ser Lys Glu Met Ala Gln His Phe Lys Ser
                35                   40

Lys Asn Val Asp Val Tyr Pro Ile Arg Tyr
                45                   50

Ser Ile Asn Cys Tyr Gly Gly Glu Ile Asp
                55                   60

Arg Thr Ala Cys Thr Tyr Gly Gly Val Thr
                65                   70

Pro His Glu Gly Asn Lys Leu Lys Glu Arg
                75                   80

Lys Lys (2) INFORMATION FOR SEQ ID NO: 19:

(i) SEQUENCE CHARACTERISTICS:
        (A) LENGTH: 82
        (B) TYPE: Amino Acid
        (C) STRANDEDNESS: Unknown
        (D) TOPOLOGY: Unknown (ii) MOLECULE TYPE: Peptide (xi) SEQUENCE DESCRIPTION: SEQ ID NO: 19:

Ser Asp Asp Gln Phe Leu Glu Asn Thr Leu
                 5                   10

Leu Phe Lys Gly Phe Phe Thr Gly His Pro
                15                   20

Trp Tyr Asn Asp Leu Leu Val Asp Leu Gly
                25                   30

Ser Lys Asp Ala Thr Asn Lys Tyr Lys Gly
                35                   40

Lys Lys Val Asp Leu Tyr Gly Ala Tyr Tyr
                45                   50

Gly Tyr Gln Cys Ala Gly Gly Thr Pro Asn
                55                   60

Lys Thr Ala Cys Met Tyr Gly Gly Val Thr
                65                   70

Leu His Asp Asn Asn Arg Leu Thr Glu Glu
                75                   80

Lys Lys (2) INFORMATION FOR SEQ ID NO: 20:

(i) SEQUENCE CHARACTERISTICS:
        (A) LENGTH: 89
        (B) TYPE: Amino Acid
        (C) STRANDEDNESS: Unknown
        (D) TOPOLOGY: Unknown (ii) MOLECULE TYPE: Peptide (xi) SEQUENCE DESCRIPTION: SEQ ID NO: 20:

Ser Ile Asp Gln Phe Leu Tyr Phe Asp Leu
                 5                   10

Ile Tyr Ser Ile Lys Asp Thr Lys Leu Gly
                15                   20

Asn Tyr Asp Asn Val Arg Val Glu Phe Lys
                25                   30

Asn Lys Asp Leu Ala Asp Lys Tyr Lys Asp
```

```
                    35                  40
Lys Tyr Val Asp Val Phe Gly Ala Asn Tyr
                    45                  50

Tyr Gln Cys Tyr Phe Ser Lys Lys Thr Asn
                    55                  60

Asp Ile Asn Ser His Gln Thr Asp Lys Arg
                    65                  70

Lys Thr Cys Met Tyr Gly Gly Val Thr Glu
                    75                  80

His Asn Gly Asn Gln Leu Asp Lys Tyr
                    85
```

(2) INFORMATION FOR SEQ ID NO: 21:

(i) SEQUENCE CHARACTERISTICS:
        (A) LENGTH: 89
        (B) TYPE: Amino Acid
        (C) STRANDEDNESS: Unknown
        (D) TOPOLOGY: Unknown (ii) MOLECULE TYPE: Peptide (xi) SEQUENCE DESCRIPTION: SEQ ID NO: 21:

```
Ser Val Asp Lys Phe Leu Ala His Asp Leu
                    5                   10

Ile Tyr Asn Ile Ser Asp Lys Lys Leu Lys
                    15                  20

Asn Tyr Asp Lys Val Lys Thr Glu Leu Leu
                    25                  30

Asn Glu Gly Leu Ala Lys Lys Tyr Lys Asp
                    35                  40

Glu Val Val Asp Val Tyr Gly Ser Asn Tyr
                    45                  50

Tyr Val Asn Cys Tyr Phe Ser Ser Lys Asp
                    55                  60

Asn Val Gly Lys Val Thr Gly Gly Lys Thr
                    65                  70

Cys Met Tyr Gly Gly Ile Thr Lys His Glu
                    75                  80

Gly Asn His Phe Asp Asn Gly Asn Leu
                    85
```

(2) INFORMATION FOR SEQ ID NO: 22:

(i) SEQUENCE CHARACTERISTICS:
        (A) LENGTH: 89
        (B) TYPE: Amino Acid
        (C) STRANDEDNESS: Unknown
        (D) TOPOLOGY: Unknown (ii) MOLECULE TYPE: Peptide (xi) SEQUENCE DESCRIPTION: SEQ ID NO: 22:

```
Ser Val Asp Lys Phe Leu Ala His Asp Leu
                    5                   10

Ile Tyr Asn Ile Ser Asp Lys Lys Leu Lys
                    15                  20

Asn Tyr Asp Lys Val Lys Thr Glu Leu Leu
                    25                  30
```

```
Asn Glu Asp Leu Ala Lys Lys Tyr Lys Asp
            35                  40

Glu Val Val Asp Val Tyr Gly Ser Asn Tyr
            45                  50

Tyr Val Asn Cys Tyr Phe Ser Ser Lys Asp
            55                  60

Asn Val Gly Lys Val Thr Gly Gly Lys Thr
            65                  70

Cys Met Tyr Gly Gly Ile Thr Lys His Glu
            75                  80

Gly Asn His Phe Asp Asn Gly Asn Leu
            85
```

(2) INFORMATION FOR SEQ ID NO: 23:

(i) SEQUENCE CHARACTERISTICS:
        (A) LENGTH: 89
        (B) TYPE: Amino Acid
        (C) STRANDEDNESS: Unknown
        (D) TOPOLOGY: Unknown (ii) MOLECULE TYPE: Peptide (xi) SEQUENCE DESCRIPTION: SEQ ID NO: 23:

```
Ser Val Asp Lys Phe Leu Ala His Asp Leu
            5                   10

Ile Tyr Asn Ile Ser Asp Lys Lys Leu Lys
            15                  20

Asn Tyr Asp Lys Val Lys Thr Glu Leu Leu
            25                  30

Asn Glu Asp Leu Ala Lys Lys Tyr Lys Asp
            35                  40

Glu Val Val Asp Val Tyr Gly Ser Asn Tyr
            45                  50

Tyr Val Asn Cys Tyr Phe Ser Ser Lys Asp
            55                  60

Asn Val Gly Lys Val Thr Gly Gly Lys Thr
            65                  70

Cys Met Tyr Gly Gly Ile Thr Lys His Glu
            75                  80

Gly Asn His Phe Asp Asn Gly Asn Leu
            85
```

(2) INFORMATION FOR SEQ ID NO: 24:

(i) SEQUENCE CHARACTERISTICS:
        (A) LENGTH: 79
        (B) TYPE: Amino Acid
        (C) STRANDEDNESS: Unknown
        (D) TOPOLOGY: Unknown (ii) MOLECULE TYPE: Peptide (xi) SEQUENCE DESCRIPTION: SEQ ID NO: 24:

```
Ser Val Asp Gln Leu Leu Ser His Asp Leu
            5                   10

Ile Tyr Asn Val Ser Gly Pro Asn Tyr Asp
            15                  20

Lys Leu Lys Thr Glu Leu Lys Asn Gln Glu
            25                  30
```

```
Met Ala Thr Leu Phe Lys Asp Lys Asn Val
                 35                  40

Asp Ile Tyr Gly Val Glu Tyr Tyr His Leu
                 45                  50

Cys Tyr Leu Cys Glu Asn Ala Glu Arg Ser
                 55                  60

Ala Cys Ile Tyr Gly Gly Val Thr Asn His
                 65                  70

Glu Gly Asn His Leu Glu Ile Pro Lys
                 75

(2) INFORMATION FOR SEQ ID NO: 25:

(i) SEQUENCE CHARACTERISTICS:
        (A) LENGTH: 73
        (B) TYPE: Amino Acid
        (C) STRANDEDNESS: Unknown
        (D) TOPOLOGY: Unknown (ii) MOLECULE TYPE: Peptide (xi) SEQUENCE DESCRIPTION: SEQ ID NO: 25:

Val Leu Asp Asn Ser Leu Gly Ser Met Arg
                 5                   10

Ile Lys Asn Thr Asp Gly Ser Ile Ser Leu
                 15                  20

Ile Ile Phe Pro Ser Pro Tyr Tyr Ser Pro
                 25                  30

Ala Phe Thr Lys Gly Glu Lys Val Asp Leu
                 35                  40

Asn Thr Lys Arg Thr Lys Lys Ser Gln His
                 45                  50

Thr Ser Glu Gly Thr Tyr Ile His Phe Gln
                 55                  60

Ile Ser Gly Val Thr Asn Thr Glu Lys Leu
                 65                  70

Pro Thr Pro
```

BACTERIAL SUPERANTIGEN VACCINES

This application is a divisional application of U.S. patent application Ser. No. 08/882,431, filed Jun. 25, 1997, now U.S. Pat. No. 6,713,284, issued Mar. 30, 2004.

Staphylococcal enterotoxins (SEs) A through E are the most commom cause of food poisoning [Bergdoll, M. S. (1983) In Easom CSF, Aslam C., eds. *Staphylococci and staphylococcal infections*. London: Academic Press, pp 559-598] and are associated with several serious diseases [Schlievert, P. M. (1993) *J. Infect. Dis.* 167: 997-1002; Ulrich et al. (1995) *Trends Microbiol.* 3: 463-468], such as bacterial arthritis [Schwab et al. (1993) *J. Immunol.* 150; 4151-4159; Goldenberg et al. (1985) *N. Engl. J. Med.* 312: 764-771], other autoimmune disorders [Psnett, D. N. (1993) *Semin. Immunol.* 5: 65-72], and toxic shock syndrome [Schlieverst, P. M. (1986) Lancet 1: 1149-1150; Bohach et al. (1990) *Crit. Rev. Microbiol.* 17: 251-272]. The non-enterotoxic staphylococcal superantigen toxic shock syndrome toxin-1 (TSST-1) was first identified as a causative agent of menstrual-associated toxic shock syndrome [Schlievert et al. (1981) *J. Infect. Dis.* 143: 509-516]. Superantigen-producing *Staphylococcus aureus* strains are also linked to Kawasaki syndrome, an inflammatory disease of children [Leung et al. (1993) *Lancet* 342: 1385-1388].

The staphylococcal enterotoxins A-E, toxic shock syndrome toxin-1 (TSST-1), and streptococcal pyrogenic exotoxins A-C are soluble 23-29-kD proteins commonly referred to as bacterial superantigens (SAgs). Bacterial superantigens are ligands for both major histocompatibility complex (MHC) class II molecules, expressed on antigen-presenting cells, and the variable portion of the T cell antigen receptor β chain (TCR Vβ) [Choi et al. (1989) *Proc. Natl. Acad. Sci. USA* 86:8941-8945; Fraser, J. D. (1989) *Nature* 339:221-223; Marrack et al. (1990) *Science* 248: 705-711; Herman et al. (1991) *Annu. Rev. Immunol.* 9: 745-772; Mollick et al. (1989) *Science* 244:817-820].

Each bacterial superantigen has a distinct affinity to a set of TCR Vβ, and coligation of the MHC class II molecule polyclonally stimulates T cells [White et al. (1989) Cell 56: 27-35; Kappler et al. (1989) *Science* 244: 811-813; Takimoto et al. (1990) *Eur J. Immunol.* 140: 617-621]. Pathologically elevated levels of cytokines that are produced by activated T cells are the probable cause of toxic shock symptoms [Calson et al. (1985) *Cell. Immunol.* 96: 175-183; Stiles et al. (1993) *Infect. Immun.* 61: 5333-5338]. In addition, susceptibility to lethal gram-negative endotoxin shock is enhanced by several bacterial superantigens [Stiles, et al., supra]. Although antibodies reactive with superantigens are present at low levels in human sera [Takei et al. (1993) *J. Clin. Invest.* 91: 602-607], boosting antibody titers by specific immunization may be efficacious for patients at risk for toxic shock syndrome and the other disorders of common etiology.

A vaccine approach to controlling bacterial superantigen-associated diseases presents a unique set of challenges. Acute exposure to bacterial superantigens produces T cell anergy, a state of specific non-responsiveness [Kawabe et al. (1991) *Nature* 349: 245-248], yet T cell help is presumably a requirement for mounting an antibody response.

Presently, the only superantigen vaccines available are chemically inactivated toxoids from different bacteria which have several disadvantages. The chemical inactivation process can be variable for each production lot making the product difficult to characterize. The chemical used for inactivation, (e.g. formaldehyde), is often toxic and does not negate the possibility of reversion of the inactivated superantigen to an active form. In addition, the yields of wild-type toxin from bacterial strains used for making toxoids are often low.

SUMMARY OF THE INVENTION

The present invention relates to a vaccine which overcomes the disadvantages of the chemically inactivated toxoids described above. The superantigen vaccine(s) of the present invention is/are designed to protect individuals against the pathologies resulting from exposure to one or several related staphylococcal and streptococcal toxins. The superantigen vaccine is comprised of a purified protein product that is genetically attenuated by DNA methodologies such that superantigen attributes are absent, however the superantigen is effectively recognized by the immune system and an appropriate antibody response is produced.

Specifically, the vaccine of the present invention is a product of site-directed mutagenesis of the DNA coding sequences of superantigen toxins resulting in a disruption of binding to both the MHC class II receptor and to the T-cell antigen receptor. A comprehensive study of the relationships of the superantigen structures of TSST-1, streptococcal pyrogenic exotoxin-A (SPEa), staphylococcal enterotoxin B (SEB), and staphylococcal enterotoxin A, to receptor binding were undertaken to provide insight into the design of the vaccine. From these studies, critical amino acid residues of the toxin responsible for binding the superantigen to the human MHC receptor were defined. Site-directed mutagenesis of the gene encoding the toxin and expression of the new protein product resulted in a superantigen toxin with disrupted binding to the MHC receptors.

Therefore, it is an object of the present invention to provide a superantigen toxin DNA fragment which has been genetically altered such that binding of the encoded altered toxin to the MHC class II or T-cell antigen receptor is disrupted. Such a DNA fragment is useful in the production of a vaccine against superantigen toxin infections.

It is another object of the present invention to provide a superantigen toxin amino acid sequence which has been altered such that the binding of the encoded altered toxin to the MHC class II or T-cell antigen receptor is disrupted. Such a sequence is useful for the production of a superantigen toxin vaccine.

It is another object of the invention to provide a recombinant vector comprising a vector and the DNA fragment described above.

It is a further object of the present invention to provide host cells transformed with the above-described recombinant DNA constructs. Host cells include cells of other prokaryotic species or eukaryotic plant or animal species, including yeasts, fungi, plant culture, mammalian and non-mammalian cell lines, insect cells and transgenic plants or animals.

It is another object of the present invention to provide a method for producing altered superantigen toxin with disrupted MHC class II and T-cell antigen receptor binding which comprises culturing a host cell under conditions such that a recombinant vector comprising a vector and the DNA fragment described above is expressed and altered superantigen toxin is thereby produced, and isolating superantigen toxin for use as a vaccine against superantigen toxin-associated bacterial infections and as a diagnostic reagent.

It is still another object of the invention to provide a purified altered superantigen toxin useful as a vaccine and as a diagnostic agent.

It is another object of the invention to provide a purified altered superantigen toxin for the therapeutic stimulation of, or other in vivo manipulation of, selective T cell subsets, or ex vivo manipulation of T cells for in vivo therapeutic purposes in mammals. Diseases, such as autoimmunity, wherein T-cell responses of limited diversity (oligoclonal) are evident. Altered superantigens may be used to therapeutically inactivate (induce anergy in) T cells in diseases wherein oligoclonal T-cell responses are evident such as autoimmune diseases, for example. For diseases in which specific T-cell subsets are not active or are anergetic, altered superantigens may be used to therapeutically stimulate these T cells. Such disease include, but are not limited to, infectious diseases and cancers wherein specific subsets of cytotoxic or helper T cells are inactivated or are otherwise unable to respond normally to the antigenic stimulation of the disease moiety.

It is a further object of the present invention to provide an antibody to the above-described altered superantigen toxin for use as a therapeutic agent, and as a diagnostic agent.

It is yet another object of the invention to provide a superantigen toxin vaccine comprising an altered superantigen toxin effective for the production of antigenic and immunogenic response resulting in the protection of an animal against superantigen toxin infection.

It is a further object of the invention to provide a multivalent superantigen toxin vaccine comprising altered toxins from a variety of streptococcal and staphylococcal toxins effective for the production of antigenic and immunogenic response resulting in the protection of an animal against infection with bacterial superantigen toxin-expressing strains and against other direct or indirect exposures to bacterial superantigen toxins such as might occur by ingestion, inhalation, injection, transdermal or other means.

It is yet another object of the present invention to provide a method for the diagnosis of superantigen toxin-associated bacterial infection comprising the steps of:

(i) contacting a sample from an individual suspected of having a superantigen toxin-associated bacterial infection with antibodies which recognize superantigen toxin using antibodies generated from the altered superantigen toxin; and (ii) detecting the presence or absence of a superantigen-associated bacterial infection by detecting the presence or absence of a complex formed between superantigen toxin in said sample and antibodies specific therefor.

It is yet another object of the present invention to provide a method for the diagnosis of superantigen bacterial infection comprising the steps of:

(i) contacting a sample from an individual suspected of having the disease with lymphocytes which recognize superantigen toxin produced by said superantigen bacteria or lymphocytes which recognize altered superantigen toxin; and (ii) detecting the presence or absence of responses of lymphocytes resulting from recognition of superantigen toxin. Responses can be, for example, measured cytokine release, increase of activation markers, mitotic activity, or cell lysis. The lymphocytes responding to the altered superantigen toxins recognize them as recall antigens not as superantigens, therefore the response is an indicator of prior exposure to the specific superantigen. The absence of a response may indicate no prior exposure, a defective immune response or in some cases a manifestation of T-cell anergy. Anergy is defined here as antigen-specific or a generalized non-responsiveness of subsets of T cells.

It is a further object of the present invention to provide a diagnostic kit comprising an antibody against an altered superantigen toxin and ancillary reagents suitable for use in detecting the presence of superantigen toxin in animal tissue or serum.

It is another object of the present invention to provide a detection method for detecting superantigen toxins or antibodies to superantigen toxin in samples, said method comprising employing a biosensor approach. Such methods are known in the art and are described for example in Karlsson et al. (1991) *J. Immunol. Methods* 145, 229-240 and Jonsson et al. (1991) *Biotechniques* 11, 620-627.

It is yet another object of the present invention to provide a therapeutic method for the treatment or amelioration of symptoms of superantigen-associated bacterial infection, said method comprising providing to an individual in need of such treatment an effective amount of sera from individuals immunized with one or more altered superantigen toxins from different bacteria in a pharmaceutically acceptable excipient.

It is further another object of the present invention to provide a therapeutic method for the treatment or amelioration of symptoms of superantigen toxin-associated bacterial infection, said method comprising providing to an individual in need of such treatment an effective amount of antibodies against altered superantigen toxins in a pharmaceutically acceptable excipient.

It is another object of the present invention to provide a therapeutic method for the treatment or amelioration of symptoms of bacterial superantigen toxin infection, said method comprising providing to an individual in need of such treatment an effective amount of altered superantigen from a variety of streptococcal and staphylococcal bacteria in order to inhibit adhesion of superantigen bacterial toxin to MHC class II or T-cell receptors by competitive inhibition of these interactions.

It is yet another object of the present invention to provide a therapeutic method for the treatment of diseases that may not be associated directly with superantigen toxins but which result in specific nonresponsiveness of T-cell subsets, said method comprising the administration of altered superantigen toxins, in vivo or ex vivo, such that T-cell subsets are expanded or stimulated. Diseases which cause anergy or nonresponsiveness of T-cells include, but are not limited to, infectious diseases.

It is another object of the present invention to provide a therapeutic method for the treatment of diseases associated with expanded or over-stimulated T-cell subsets, such as autoimmunity for example, said method comprising administration of altered superantigen toxin, in vivo or ex vivo, such that anergy or inactivation of disease associated T-cells is produced. In this case, superantigen mutants can be designed with altered but not attenuated T-cell receptor binding, to cause anergy of only the select (i.e. 1-3) T-cell subsets that are pathologically activated.

BRIEF DESCRIPTION OF THE DRAWINGS

These and other features, aspects, and advantages of the present invention will become better understood with reference to the following description and appended claims, and accompanying drawings where:

FIG. 1. Staphylococcal and streptococcal superantigen amino acid sequence homologies, compiled with Genetics Computers Group of Univ. of Wisconsin software.

A. SEB mutant HLA-DR1-binding; B. SEA mutant HLA-DR1-binding; C. T-cell recognition of SEA and SEB mutants. Binding of bacterial superantigens to cell surface DR1 was measured by laser fluorescence-activated flow cytometry. A representative experiment of three performed is shown. The mutants SEA D197N, the homologous SEB D199N, and SEA L11Y had no effect on binding or T-cell recognition, and were used for controls. Human T-cell proliferation, assessed by [$^3$H]thymidine incorporation, was measured in response to SEA (Y64A) or SEB (Y61A) mutants and controls that retained DR1-binding affinities. Each data point represents the mean of triplicate determinations; SEM<5%.

FIG. 3. Sequence and secondary structural alignment of bacterial superantigen toxins. Analyses were performed with the applications PILEUP and PROFILE from the Computer Genetics Group (Madison, Wis.) using sequence data obtained from a variety of sources. Amino acid residue numbering is based on the SEA sequence. (SEQ ID NOS: 17-25).

FIG. 4. Detection of TNF-α (a), IL-1α (B), IL-6 (C) and IFN-γ (D) in the serum of mice injected with SEA (open circles), LPS (open triangles), or SEA plus LPS (open squares). Values for TNF-α and IL-1α represent the mean of duplicate samples, with an SEM of ±5%. INF-γ and IL-6 values represent the mean of duplicate and triplicate samples, respectively. The SEMs for IFN-γ and IL-6 readings were ±5% and ±10%, respectively.

Figure 5:
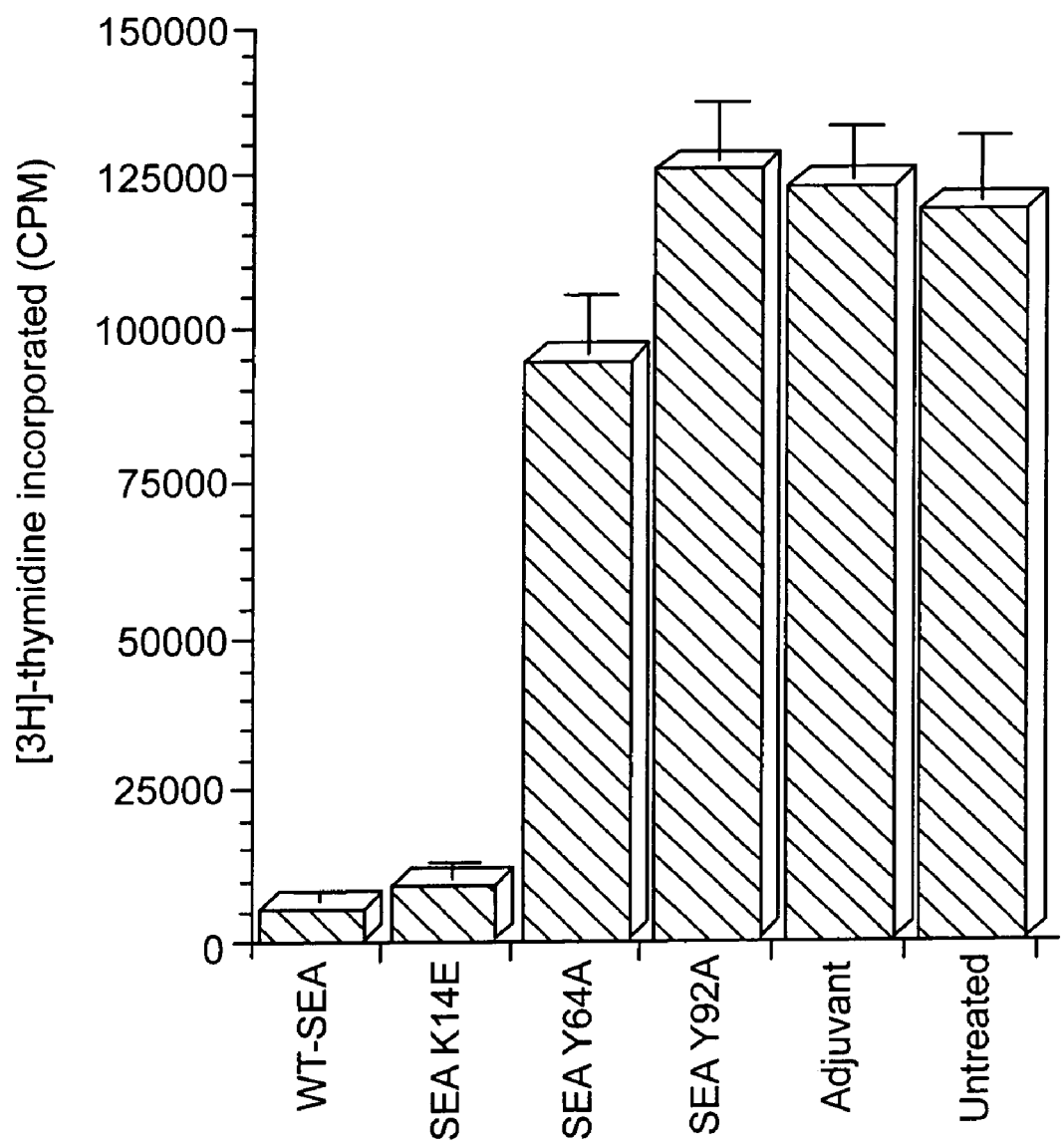

FIG. 5. Mutant SEA vaccines that have attenuated major histocompatibility complex class II or T-cell antigen receptor binding do not induce T-cell anergy. Mice were given three doses of wild type (WT) SEA or site-specific mutant vaccine, plus adjuvant. Control animals received adjuvant alone or were untreated; 2 weeks after final injection, pooled mononuclear cells were collected from spleens of 4 mice from each group. Results are represented as mean cpm (±SD) of quadruplicate wells incubated with 100 ng/ml WT SEA for 72 h and then pulse-labeled for 12 h with [$^3$H] thymidine. P<0.0001 (analysis of variance for repeated measures comparing untreated, adjuvant, Y64A, and Y92A to WT SEA group).

FIG. 6. No superantigen-induced T-cell anergy is exhibited by rhesus monkeys immunized with the vaccine B899445. Peripheral blood lymphocytes were incubated with titrated concentrations of wild-type superantigens from individual rhesus monkeys (k422 and N103) that were immunized with B899445. T-cell proliferation was assessed by [$^3$H]thymidine incorporation. Each data point represents the mean of triplicate determinations; SEM<5%.

Figure 7:
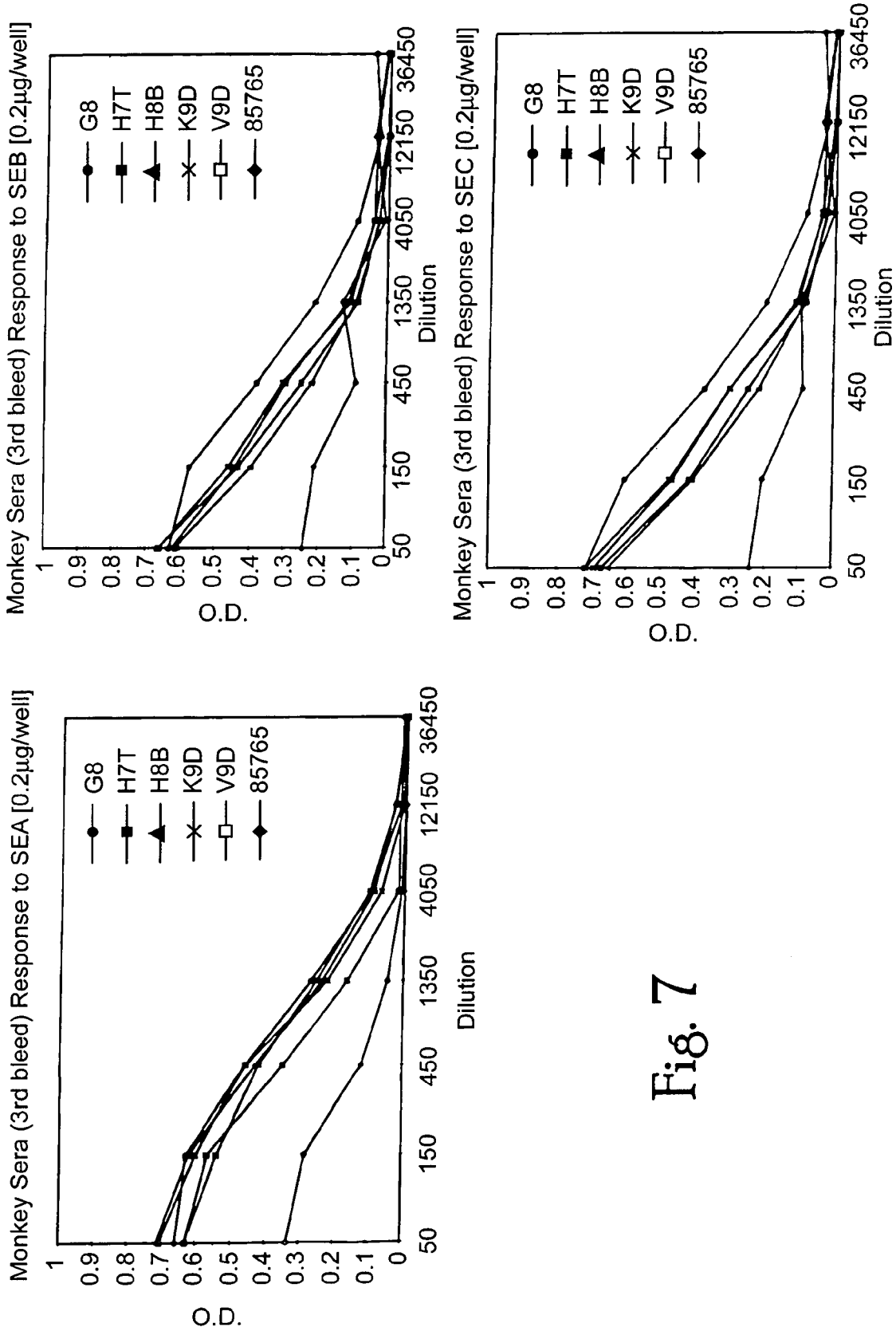

FIG. 7. Antibody responses of rhesus monkeys immunized with a combined vaccine consisting of B899445 (SEB) and A489270 (SEA). The antibody levels were measured by ELISA, using plates coated with SEA, SEB or SEC1 as listed. Monkey G8 is a non-immunized control. SEM<5% for triplicate measurements.

DETAILED DESCRIPTION

The present invention relates in part to a vaccine against superantigen toxin-associated bacterial diseases. The superantigen vaccines used in this study were developed by engineering changes in the receptor-binding portions of superantigen toxins to reduce receptor-binding affinities and toxicity while maintaining antigenicity.

Five different superantigen vaccines are described in this application: staphylococcal enterotoxin A, staplylococcal enterotoxin B, staphylococcal enterotoxin C1, toxic-shock syndrome toxin-1, and streptococcal pyrogenic exotoxin-A. For each of the superantigen toxins above, a comprehensive study of the relationships of the toxin protein structure to receptor binding was undertaken to provide insight into the design of the vaccine. The study employed site-directed mutagenesis of toxin and receptor molecules, molecular modeling, protein structure and binding studies. Following these studies, toxins were altered by site-directed mutagenesis to attenuate MHC class II binding and biological activity to an essentially non-specific level. The engineered vaccines were evaluated at each stage of analysis to determine mouse and human T-cell reactivities in vitro, serological responses and toxicity in mice and monkeys.

In one embodiment, the present invention relates to an altered superantigen toxin protein having an amino acid sequence which has been altered such that the binding of the toxin to the MHC class II receptor is disrupted.

For the invention described below, the following sequence identifiers may be used to refer to certain nucleotide or amino acid sequences. SEQ ID NO:1 refers to a DNA sequence of Staphylococcal enterotoxin A vaccine, periplasmic (A489270P); SEQ ID NO:2 refers to an amino acid sequence of Staphylococcal enterotoxin A vaccine, periplasmic (A489270P); SEQ ID NO:3 refers to a DNA sequence of Staphylococcal enterotoxin A vaccine, cytoplasmic (A489270C); SEQ ID NO:4 refers to an amino acid sequence of Staphylococcal enterotoxin A vaccine, cytoplasmic (A489270C); SEQ ID NO:5 refers to a DNA sequence of Staphylococcal enterotoxin B vaccine (B42360210); SEQ ID NO:6 refers to an amino sequence of Staphylococcal enterotoxin B vaccine (B42360210); SEQ ID NO:7 refers to a DNA sequence of Staphylococcal enterotoxin B vaccine, periplasmic (B899445P); SEQ ID NO:8 refers to an amino sequence of Staphylococcal enterotoxin B vaccine, periplasmic (B899445P); SEQ ID NO:9 refers to a DNA sequence of Staphylococcal enterotoxin B vaccine, cytoplasmic (B899445C); SEQ ID NO:10 refers to an amino acid sequence of Staphylococcal enterotoxin B vaccine, cytoplasmic (B899445C); SEQ ID NO:11 refers to a DNA sequence for Staphylococcal toxic shock syndrome toxin-1 vaccine (TST30); SEQ ID NO:12 refers to an amino acid sequence for Staphylococcal toxic shock syndrome toxin-1 vaccine (TST30); SEQ ID NO:13 refers to a DNA sequence for Staphylococcal enterotoxin C1 vaccine (SEC45); SEQ ID NO:14 refers to an amino acid sequence for Staphylococcal enterotoxin C1 vaccine (SEC45); SEQ ID NO:15 refers to a DNA sequence for Streptococcal pyrogenic exotoxin A vaccine (SPEA42); and SEQ ID NO:16 refers to an amino acid sequence for Streptococcal pyrogenic exotoxin A vaccine (SPEA42).

Figure 1:
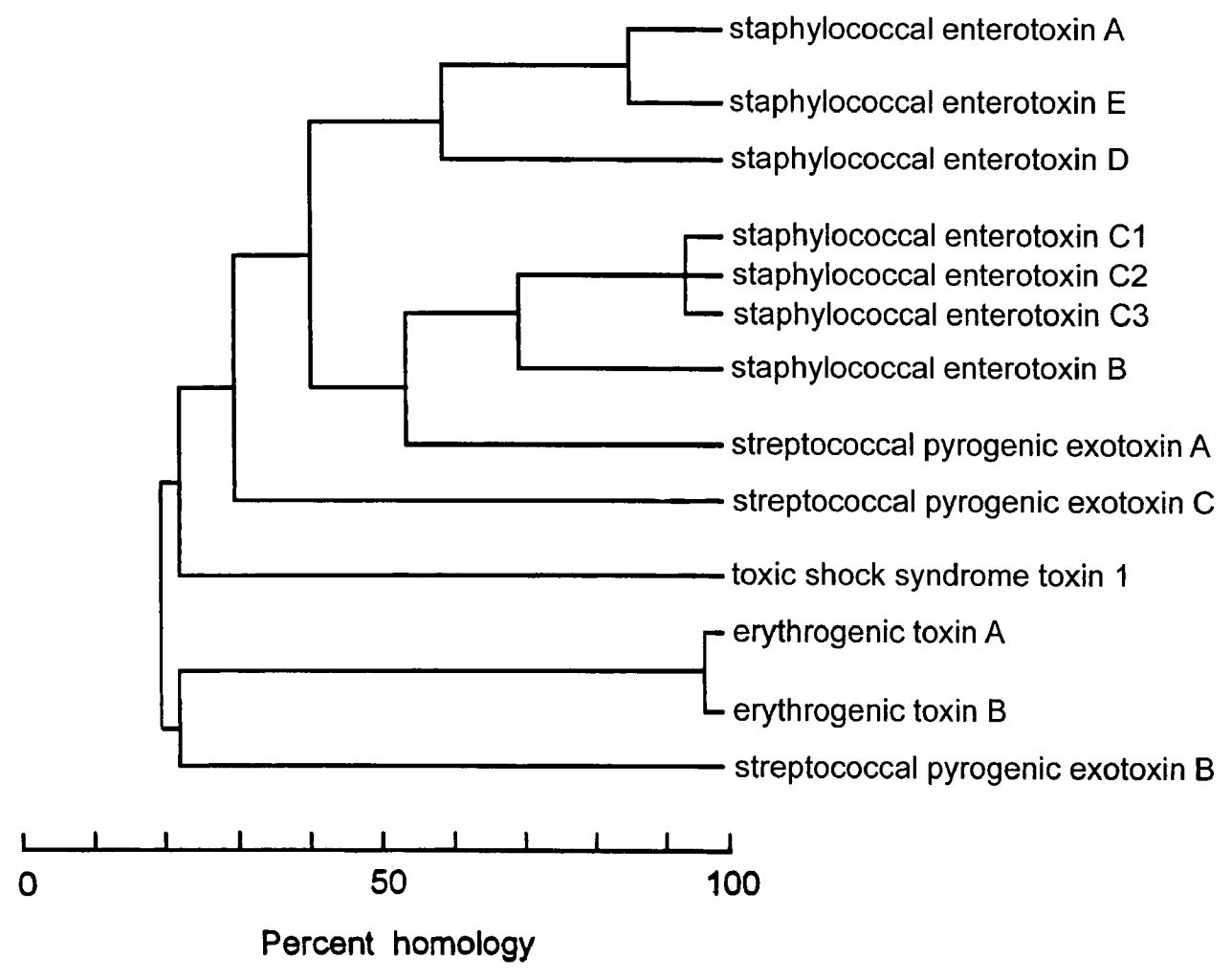

Comparison of amino acid sequences (FIG. 1) suggested that bacterial superantigens fall into groups consisting of (1) SEA, SED and SEE, (2) SEB, staphylococcal enterotoxins $C_1$-$C_3$ (SEC1-3), the streptococcal pyrogenic exotoxins A (SPE-A) and C (SPE-C), (3) TSST-1 and (4) the exfoliative toxins (ETA, ETB) and streptococcal pyrogenic exotoxin B (SPE-B), which are the most distant from the others in sequence. Although not available to the inventor when the inventions were first conceived and proof of principle was obtained, the x-ray crystallographic structures of several bacterial superantigens are now known. Diverse superantigens, such as SEB and TSST-1, appear to have little sequence in common, yet they exhibit homologous protein folds composed largely of β strands [Prasad, G. S. et al. (1993) *Biochemistry* 32, 13761-13766; Acharya, R. K. et al. (1994) *Nature* 367, 94-97; Swaminathan, S. et al. (1992) *Nature* 359, 801-806] within two distinct domains. Differences between the proteins are located primarily in highly variable regions comprised of several surface loops, such as the disulfide-bonded loop which is absent from TSST-1 and at the amino terminus.

The X-ray crystal structures of SEB and TSST-1 complexed with HLA DR1 are known [Kim, J. et al. (1994) *Science* 266, 1870-1874; Jardetzky, T. S. et al. (1994) *Nature* 368, 711-718]. The region of HLA DR1 that contacts SEB consists exclusively of α subunit surfaces. The main regions of SEB involved are two conserved sites: a polar pocket derived from three β strands of the β barrel domain and a highly solvent-exposed hydrophobic reverse turn. The polar binding pocket of SEB contains a glutamate and two tyrosines that accommodate Lys39 of the α subunit of HLA DR1, while the hydrophobic region consists of a leucine and flanking residues that make several contacts with the HLA DRα chain. The HLA DR1 binding sites of both TSST-1 and SEB overlap significantly. The hydrophobic binding contacts of other SAg with the HLA DRα chain have been proposed [Ulrich, et al. (1995). *Nature, Struct. Biol* 2, 554-560] to be similar to those found in SEB and TSST-1. A motif consisting of a leucine in a reverse turn [Ulrich et al. (1995), supra] is conserved among bacterial superantigens and may provide the key determinant (hydrophobic or otherwise) for binding HLA-DR. However, TSST-1 does not have a highly charged residue in the polar pocket that interacts with Lys39 of the HLA DRα chain and uses an alternative conformational binding mode that allows TSST-1 to interact with HLA DR1 β-chain residues and the carboxy-terminal region of the antigenic peptide.

Both SEA and SEE bind to the β subunit of DR by means of a single zinc atom [Fraser, J. D. et al. (1992) *Proc. Natl. Acad. Sci. USA* 89, 5507-5511]. The amino-terminal domain of SEA interfaces with the HLA DRα chain [Ulrich, et al. (1995)], while SEA C-terminal domain residues His187, His225 and Asp227 form a zinc-coordination complex, likely with His-81 from the β chain of an adjoining HLA DR molecule. However, our results have shown that binding of superantigen to the HLA DRβ subunit does not directly stimulate T cells [Ulrich et al. (1995) *Nature, Struct. Biol.* 2, 554-560], but increases the potential of the bound SEA to interact with the α chain of another HLA DR, thus increasing the biological potency.

A least-squares superimposition of the unbound molecules of modeled SEA and the crystal structure of SEB, aligned according to their structurally conserved α-helical and β-strand regions, exhibited a global folding pattern which is very similar. Differences between the two structures are calculated to be located primarily in loops of low sequence homologies, with the largest positional deviations occurring between structurally conserved regions of residues 18-20, 30-32, 173-181, 191-194, and the cysteine-loop region (90-111). Only one of these regions in SEB makes significant contact (residue Y94 [Y=tyrosine] in particular) with the HLA-DR1 molecule [Jardetzky, T. S. et al. (1994) *Nature* 368, 711-718).

The binding interface between SEB and HLA-DR1 consists principally of two structurally conserved surfaces located in the N-terminal domain: a polar binding pocket derived from three β-strand elements of the β-barrel domain and a hydrophobic reverse turn. The binding pocket of SEB contains residues E67 (E=Glutamic acid), Y89 (Y=Tyrosine) and Y115 (Y=tyrosine), and binds K39 (K=Lysine) of the DRα subunit. The amino acid one letter code is defined as the following: A=Alanine (Ala), I=Isoleucine (Ile), L=Leucine (Leu), M=Methionine (Met), F=Phenylalanine (Phe), P=Proline (Pro), W=Tryptophan (Trp), V=Valine (Val), N=Asparagine (Asn), C=Cysteine (Cys), Q=Glutamine (Q), G=Glycine (Gly), S=Serine (Ser), T=Threonine (Thr), Y=Tyrosine (Tyr), R=Arginine (Arg), H=Histidine (His), K=Lysine (Lys), D=Aspartic acid (Asp), and E=Glutamic acid (Glu). For SEA, the binding interface with the DR molecule is modeled to contain a similar binding pocket consisting of residues D70, Y92 and Y108. Mutation of residue Y89 in SEB or Y92 in SEA to alanine (FIG. 2) resulted in greater than 100-fold reduction in DR1 binding. The substitution of alanine for Y89 in SEB and Y92 in SEA eliminates the hydrogen bond with K39 and disrupts packing interactions with adjacent protein residues. Modeling of the SEA mutant Y92A predicts an increase in solvent-accessible surface area for Y108 by a factor of two greater than the wild-type structure, allowing the formation of a hydrogen bond to the carboxylate group of D70 and thus disrupting key anchoring and recognition points for HLA-DR1. This effect is expected to be somewhat less in SEB due to the longer side chain at E67. Substitution of SEB Y115 with alanine also resulted in greater than 100-fold reduction of binding. In contrast, the same replacement of Y108 in SEA yielded little to no change in DR1 binding (FIG. 2*a*), suggesting the primary importance of SEA residues Y92 and D70 for stabilizing interactions with K39. The K39 side chain of DRα forms a strong ion-pair interaction with the SEB E67 carboxylate group and hydrogen bonds with the hydroxyl groups of Y89 and Y115. Substitution of SEB E67 by glutamine reduced binding affinity by greater than 100-fold (FIG. 2), reflecting the replacement of the strong ionic bond with a weaker hydrogen bond. To optimize ion-pair interactions of the analogous SEA site, the shorter carboxylate side chain of D70 is predicted to shift K39 of DRα, weakening interactions with SEA Y108. The substitution of alanine for SEA Y108 is thus more easily accommodated than the homologous substitution of SEB Y115, without loss in DR1 binding.

Comparisons of the polar pocket with other bacterial superantigens were then made. SEC1-3 and SPE-A have conserved the critical DR1 binding-interface residues (FIG. 1), and share with SEB and SEA secondary structural elements of the DR1-binding surfaces. Asparagine in SED (N70) replaces the acidic side chain present in SEA, SEB, SPE-A and SEC1-3. Accordingly, for SED the salt bridge of the polar pocket is likely to be replaced by a hydrogen bond. Overall, DR1 affinities for SED and SEA appeared to be equivalent (FIG. 2*b*), indicating that other interactions may compensate for the absence in SED of the ion-pair found in the other superantigens. For the case of TSST-1, mutating DRα residues K39 to serine or M36 to isoleucine has been shown to greatly reduce binding [Panina-Bordignon et al. (1992) *J. Exp. Med.* 176: 1779-1784]. Although primarily hydrophobic, the critical TSST-1 structural elements are conserved with the SEA and SEB polar binding pocket. SEB residues Y89 and Y115 are homologous to T69 and 185 in TSST-1, respectively, and SEB E67 is replaced by I46. These TSST-1 residues are positioned in a conserved β-barrel domain found in both SEB and SEA. However, the TSST-1 site lacks polarity equivalent to SEB/SEA, and hydrogen bonding with the hydroxyl of TSST-1 residue T69 would require that DRα K39 extend 5 Å into the pocket. TSST-1 binding utilizes an alternative strategy [Kim et al. (1994) *Science* 266:1870-1874] consisting of hydrophobic contacts centered around residue I46, and potential ionic or hydrogen bonds bridging DRα residues E71 and K67 to R34 and D27, respectively, of TSST-1.

The hydrophobic region of the binding interface between SEB and the HLA-DR1 molecule consists of SEB residues 44-47, located in a large reverse turn connecting β-strands 1 and 2 of SEB. These residues appear to make strong electrostatic interactions with DRα through their backbone atoms. The mutation of L45 to an arginine reduced overall HLA-DR1 binding greater than 100-fold (FIG. 2b), attributable to the less energetically favorable insertion of a highly charged residue into a hydrophobic depression on the DR1 molecule. The modeled DR1-SEA complex presents similar interactions with the SEA backbone atoms, with the exception of a glutamine (Q49) replacing SEB Y46. Mutation of L48 to glycine in SEA (homologous to L45 of SEB) has been reported to decrease T-cell responses. SEB L45 and the comparable L30 of TSST-1 are the most extensively buried residues in the DR1 interface. The leucine is conserved among the bacterial superantigens (FIG. 3) and may provide the necessary hydrophobic structural element for surface complementarity with DR1, consistent with the mutagenesis data for SEB and SEA.

The inventor has performed similar structure and function studies with TSST-1, SEC1 and SPE-A.

Figure 2A:
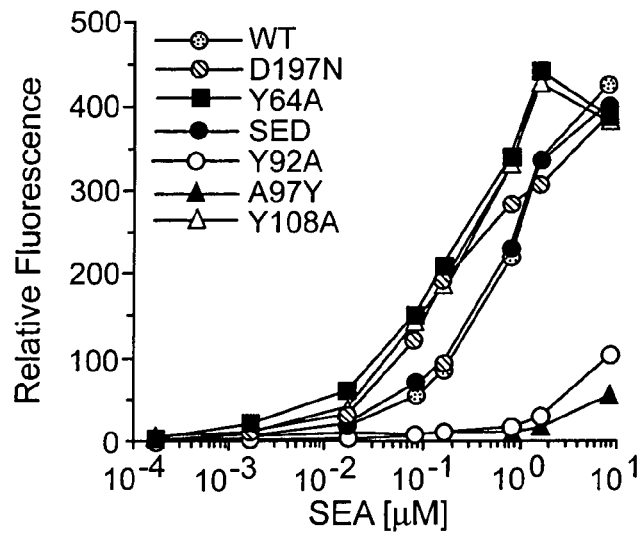
FIG. 2. Comparison of mutant SEB and SEA biological activities.

In determining the overall affinity of the superantigen for DR1, a contributory role is played by structural variations around the common binding motifs. A short, variable structured, disulfide-bonded loop is found in SEA and a homologous longer loop in SEB. The SEB residue Y94, contained within this loop, forms hydrophobic interactions with L60 and A61 of the DRα subunit. Replacement of Y94 with alanine partially inhibits DR1 binding (FIG. 2a, b). An alanine is found in SEA (A97) and SEE at the position equivalent to SEB Y94, and mutating this residue in SEA to tyrosine results in disrupted instead of stabilized interactions with DR1 (FIG. 2a). Although the disulfide loops differ in structure between SEA and SEB, A97 apparently contributes to the DRα binding interface in a manner similar to Y94 of SEB. Because TSST-1 lacks a disulfide loop, similar contacts with DRα are replaced by interactions with β-strands of TSST-1. In a like manner, the absence of a salt bridge between the residues K39 of DRα and N65 of SED is apparently compensated for by stabilizing interactions occurring outside of the otherwise conserved dominant binding surfaces (FIG. 2a).

Figure 2B:
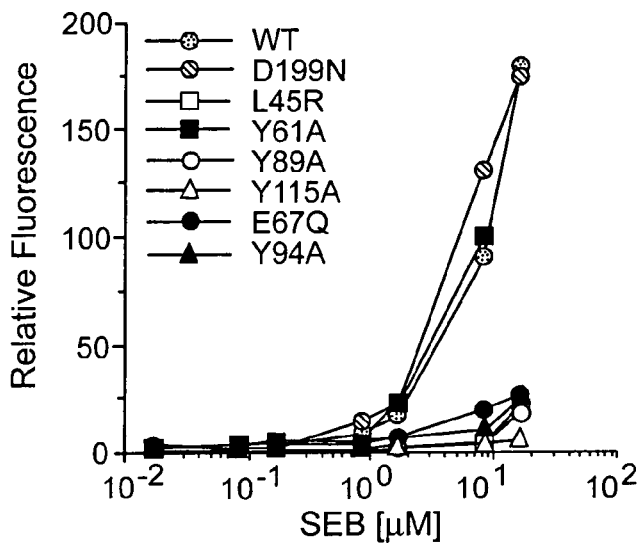
Figure 2C:
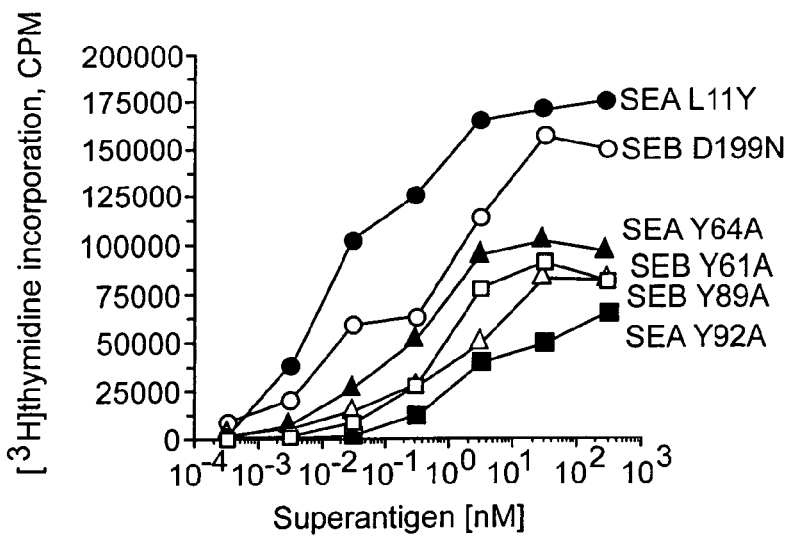
Figure 4A:
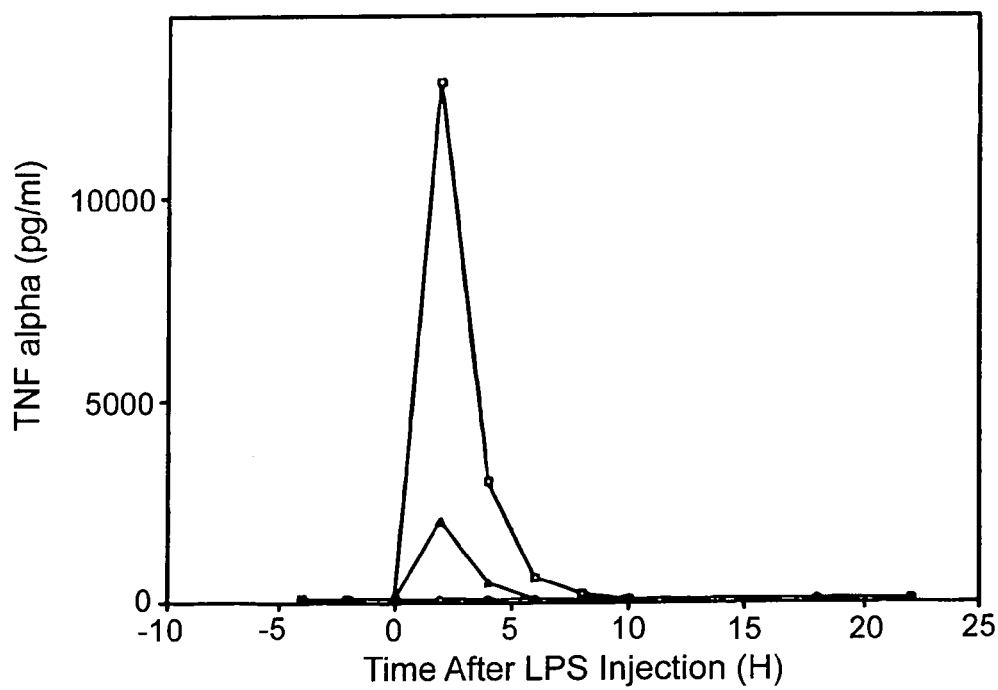
Figure 4B:
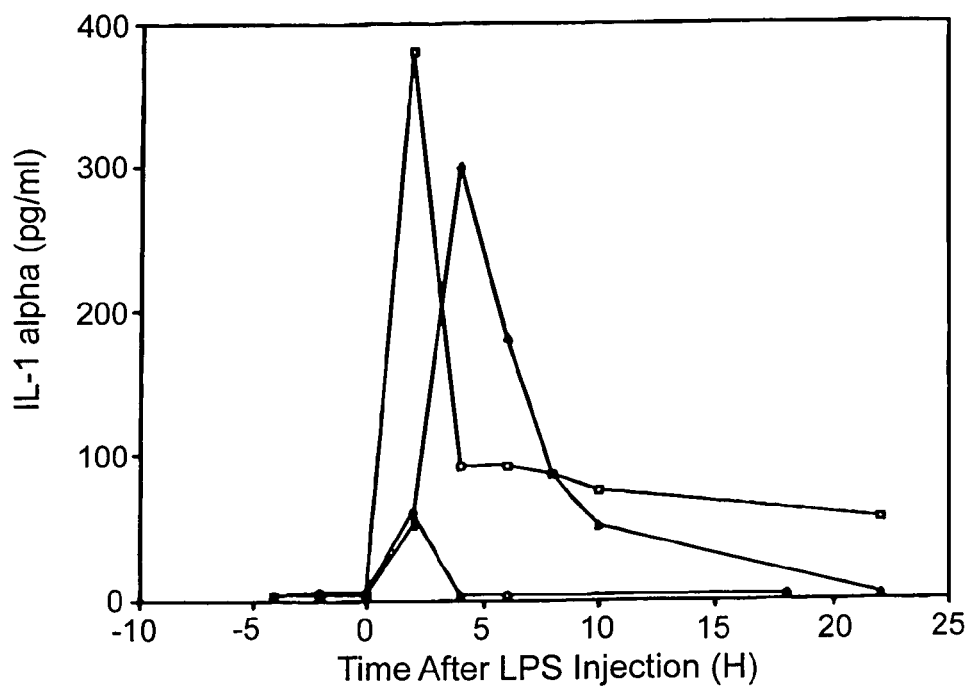
Figure 4C:
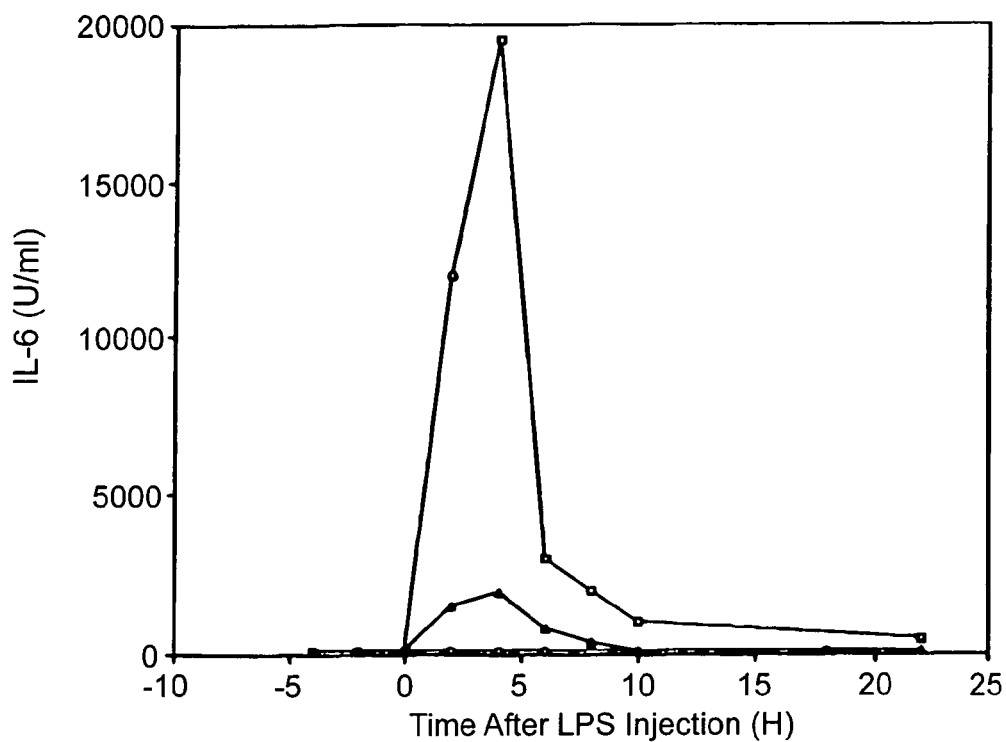
Figure 4D:
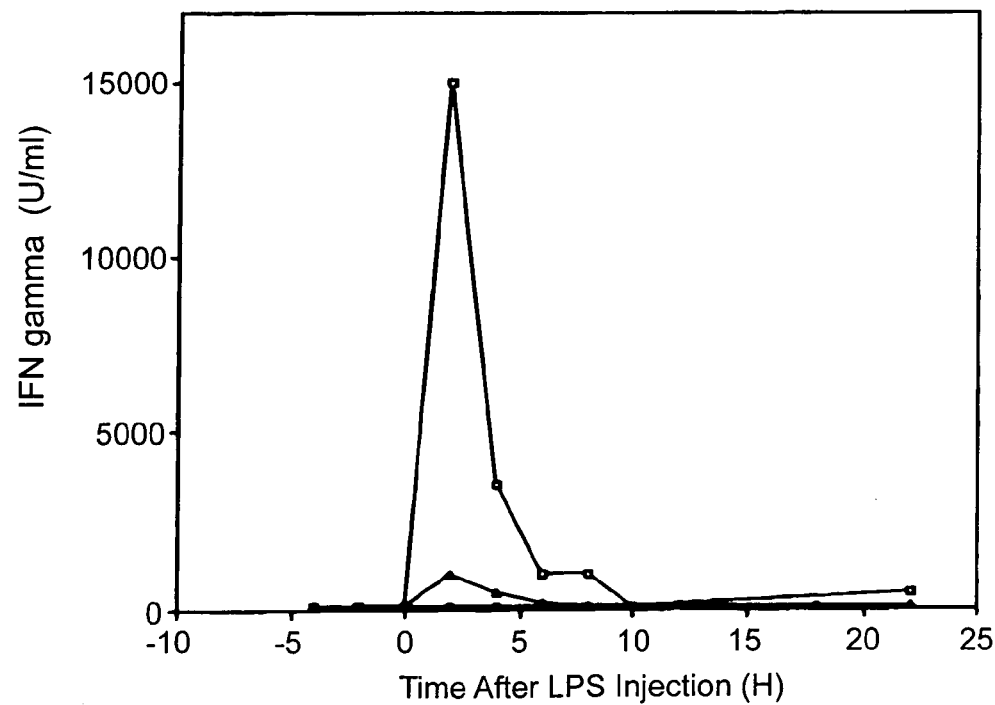

The amino acid residues in contact with TCR are located in regions of high sequence variability, presenting a unique surface for interaction with the TCR. Residues implicated in TCR interactions by mutagenesis of SEA and SEB reside in variable loop regions, while TSST-1 mutants that affect TCR binding are mainly located in an α helix [Acharya, R. K. et al. (1994) Nature 367, 94-97; Kim, J. et al. (1994) Science 266, 1870-1874]. Specifically, mutations that diminish T-cell receptor recognition of SEB include residues N23, Y61, and the homologous SEA N25 or Y64 (FIG. 2c). SEA residues S206 and $N_2O_7$ also control T-cell responses [Hudson, et al. (1992) J. Exp. Med. 177: 175-184). Mutants of the polar binding pocket, SEA Y92A and SEB Y89A, equivalently reduced T-cell responses (FIG. 2c), reflecting the observed decreases in DR1-binding (FIG. 2a, b). While supporting reduced T-cell responses, mutants SEA Y64A and SEB Y61A retained normal affinities for DR1 (FIG. 2a-c).

In view of the detailed description of the present invention and the results of molecular modelling and structural studies of staphylococcal and streptococcal superantigen toxins discussed above, any amino acid sequence derived from a superantigen toxin can be altered. Sequences of several superantigen toxins are already known and available to the public in sequence databases such as GenBank, for example. The superantigen toxin sequence is preferably altered at the hydrophobic loop or polar binding pocket depending on the superantigen. Alternatively, residues adjacent to the hydrophobic loop or polar binding pocket that contact HLA-DR or residues at sites that can indirectly alter the structure of the hydrophobic loop or polar pocket can be altered. The number of residues which can be altered can vary, preferably the number can be 1-2, more preferably 2-3, and most preferably 3-4, or more with the limitation being the ability to analyze by computational methods the consequences of introducing such mutations. The residues which can be altered can be within 5 amino acid residues of the central Leucine of the hydrophobic loop (such as L45 of SEB), or within 5 residues of one of the amino acid residues of the polar binding pocket that can contact HLA-DR, (such as E67, Y89, or Y115 of SEB), more preferably, within 3 amino acid residues of the central Leucine of the hydrophobic loop (such as L45 of SEB), or within 3 residues of one of the amino acid residues of the polar pocket that can contact HLA-DR, (such as E67, Y89, or Y115 of SEB), and most preferably, the central Leucine of the hydrophobic loop (such as L45 of SEB), or one of the amino acid residues of the polar binding pocket that can contact HLA-DR, (such as E67, Y89, or Y115 of SEB). The residues can be changed or substituted to alanine for minimal disruption of protein structure, more preferably to a residue of opposite chemical characterisitcs, such as hydrophobic to hydrophilic, acidic to neutral amide, most preferably by introduction of a residue with a large hydrated side chain such as Arginine or Lysine. In addition, side chains of certain nonconserved receptor-binding surfaces, can also be altered when designing superantigen toxins with low binding affinities. These residues can include Y94 of SEB and structurally equivalent residues of other superantigens, such as A97 of SEA, or any side chain within 5 residues from these positions or any side chain in discontinuous positions (discontinuous positions are defined as amino acid residues that fold together to form part of a discrete three-dimensional structural unit but are not present on the same secondary structural unit e.g. α helix or β-strand) such as disulfide-bonded side chains, that involve, directly or indirectly, the nonconserved receptor contact surfaces outside of the polar binding pocket or hydrophobic loop. Further, amino acid residues involved with protein folding or packing can be altered when designing superantigen toxins with low binding affinities [Sundstrom et al. (1996) EMBO J. 15, 6832-6840; Sundstrom et al. (1996) J. Biol. Chem. 271, 32212-32216; Acharya et al. (1994) Nature 367, 94-97; Prasad et al. (1993) Biochem. 32, 13761-13766; Swaminathan et al. (1992) Nature 359, 801-806]. Furthermore, especially for superantigens with higher affinities for T-cell antigen receptors, side chains of amino acids within 5 residues of the position represented by N23 (conserved residue in most superantigens), N60 (conserved Asn or Trp in most superantigens) Y91 (semiconserved hydrophobic residues Trp, Ile, Val, His in most superantigens) and D210 of SEB (conserved Asp in most superantigens) can be altered when designing superantigen toxins with low binding affinities. These residues are likely to form part of the integral molecular surfaces that are in contact with T-cell antigen receptors. Because the T-cell receptor contact areas of superantigen toxins are essential for causing specific activation or inactivation of T-cell subsets, altering residues that are unique to each superantigen but that are located within 5 residues of the positions represented by N23, N60 and Y91 can produce superantigens that affect a smaller number (e.g. 1-3) of subsets. Such altered superantigen toxins can be useful as therapeutic agents.

In another embodiment, the present invention relates to a DNA or cDNA segment which encodes a superantigen toxin such as SEA, SEB, SEC-1., SPEa., and TSST-1 to name a few, the sequence of which has been altered as described above to produce a toxin protein with altered binding ability to MHC Class II and/or T-cell receptors. For SEA, the following three mutations were introduced into the toxin molecule: Tyrosine at amino acid position 92 changed to alanine; Aspartic acid at amino acid position 70 changed to arginine; Leucine at amino acid position 48 changed to arginine. The reduction in binding to HLA DR is additive per mutation, though one or two mutations can produce a vaccine and a combination of all three mutations in one molecule produces a better vaccine. Other substitutions can also result in reduced binding.

The B899445 vaccine consists of the following three mutations simultaneously introduced into the toxin molecule: tyrosine at amino acid position 89 changed to alanine; tyrosine at amino acid position 94 changed to alanine; leucine at amino acid position 45 changed to arginine. The altered superantigen toxins can be expressed either as a full-length propolypeptide or as a polypeptide in which the leader peptide has been deleted. The full-length expressed product (SEA vaccine, A489270P; SEB vaccine B899445P, B2360210P) is secreted into the periplasmic space of E. coli host cells, and the leader peptide is recognized and cleaved by a native bacterial enzymatic mechanism. The altered superantigen toxins in which the leader peptide has been deleted (A489270C, B899445c), the first residue of the mature protein is encoded by the transcriptional start site and codon for methionine (ATG), and the protein is expressed as a nonsecreted product within the host E. coli cell. For the TSST-1 vaccine TST30, the leucine at position 30 was changed to arginine. For the SEC1 vaccine, SEC45, the leucine at position 45 was changed to arginine. For the SPE-A vaccine, SPEA42, the leucine at position 42 was changed to arginine.

In another embodiment, the present invention relates to a recombinant DNA molecule that includes a vector and a DNA sequence as described above. The vector can take the form of a plasmid such as any broad host range expression vector for example pUC18/19, pSE380, pHIL, pET21/24 and others known in the art. The DNA sequence is preferably functional linked to a promoter such that the gene is expressed when present in an expression system and an altered superantigen toxin is produced. The expression sys can be an in vitro expression system or host cells such as prokaryotic cells, or in vivo such as DNA vaccines.

In a further embodiment, the present invention relates to host cells stably or transiently transformed or transfected with the above-described recombinant DNA constructs. The host can be any eukaryotic or prokaryotic cell including but not limited in E. coli DH5α or BL21. The vector containing the altered superantigen toxin gene is expressed in the host cell and the product of the altered toxin gene, whether a secreted mature protein or a cytoplasmic product, can be used as a vaccine or as a reagent in diagnostic assays or detection methods, or for therapeutic purposes. Please see e.g., Maniatis, Fitsch and Sambrook, *Molecular Cloning; A Laboratory Manual* (1982) or *DNA Cloning*, Volumes I and II (D. N. Glover ed. 1985) for general cloning methods. The DNA sequence can be present in the vector operably linked to a highly purified IgG molecule, an adjuvant, a carrier, or an agent for aid in purification of altered toxin. The transformed or transfected host cells can be used as a source of DNA sequences described above. When the recombinant molecule takes the form of an expression system, the transformed or transfected cells can be used as a source of the altered toxin described above.

A recombinant or derived altered superantigen toxin is not necessarily translated from a designated nucleic acid sequence; it may be generated in any manner, including for example, chemical synthesis, or expression of a recombinant expression system. In addition the altered toxin can be fused to other proteins or polypeptides for directing transport for example into the periplasm or for secretion from the cell. This includes fusion of the recombinant or derived altered superantigen to other vaccines or sequences designed to aid in purification, such as His-tagged, epitope-tagged or antibody Fc-fusions.

In a further embodiment, the present invention relates to a method of producing altered superantigen toxin which includes culturing the above-described host cells, under conditions such that the DNA fragment is expressed and a superantigen toxin protein is produced. The superantigen toxin can then be isolated and purified using methodology well known in the art such as immunoaffinity chromatography or preparative isoelectric focusing. However, the method of purification is not critical to the performance of the vaccine. The altered superantigen toxin can be used as a vaccine for immunity against infection with bacterial superantigen toxins or as a diagnostic tool for detection of superantigen toxin-associated disease or bacterial infection. The transformed host cells can be used to analyze the effectiveness of drugs and agents which affect the binding of superantigens to MHC class II or T-cell antigen receptors. Chemically derived agents, host proteins or other proteins which result in the down-regulation or alteration of expression of superantigen toxins or affect the binding affinity of superantigen toxins to their receptors can be detected and analyzed. A method for testing the effectiveness of a drug or agent capable of altering the binding of superantigen toxins to their receptors can be for example computer-aided rational design or combinatorial library screening, such as phage display technology.

In another embodiment, the present invention relates to antibodies specific for the above-described altered superantigen toxins. For instance, an antibody can be raised against the complete toxin or against a portion thereof. Persons with ordinary skill in the art using standard methodology can raise monoclonal and polyclonal antibodies to the altered superantigens of the present invention, or a unique portion of the altered superantigen. Materials and methods for producing antibodies are well known in the art (see for example Goding, in, *Monoclonal Antibodies: Principles and Practice*, Chapter 4, 1986). The antibodies can be used in diagnostic assays for detection of superantigen toxin-associated infection. Neutralizing antibodies can be used in a therapeutic composition for the treatment of amelioration of anergy and/or for the treatment of a superantigen toxin-associated infection.

In a further embodiment, the present invention relates to a method for detecting the presence of superantigen-associated bacterial infections in a sample. Using standard methodology well known in the art, a diagnostic assay can be constructed by coating on a surface (i.e. a solid support) for example, a microtitration plate or a membrane (e.g. nitrocellulose membrane), all or a unique portion of the altered superantigen described above, and contacting it with the serum of a person suspected of having a superantigen-associated bacterial infection. The presence of a resulting complex formed between the altered superantigen toxin and antibodies specific therefor in the serum can be detected by any of the known methods common in the art, such as fluorescent antibody spectroscopy or colorimetry. This method of detection can be used, for example, for the diagnosis of superantigen-associated bacterial infections.

In yet another embodiment, the present invention relates to a method for detecting the presence of superantigen toxin in a sample. Using standard methodology well known in the art, a diagnostic assay can be constructed by coating on a surface (i.e. a solid support) for example, a microtitration plate or a membrane (e.g. nitrocellulose membrane), antibodies specific for altered superantigen toxin, and contacting it with serum or tissue sample of a person suspected of having superantigen-associated bacterial infection. The presence of a resulting complex formed between toxin in the serum and antibodies specific therefor can be detected by any of the known methods common in the art, such as fluorescent antibody spectroscopy or colorimetry. This method of detection can be used, for example, for the diagnosis of superantigen-associated bacterial infection or disease such as food poisoning and toxic-shock syndrome or the detection of superantigen toxin in food and drink.

In another embodiment, the present invention relates to a diagnostic kit which contains altered superantigen toxin from a specific bacteria or several different superantigen toxins from bacteria and ancillary reagents that are well known in the art and that are suitable for use in detecting the presence of antibodies to superantigen toxin-associated bacteria in serum or a tissue sample. Tissue samples contemplated can be avian, fish, or mammal including monkey and human.

In yet another embodiment, the present invention relates to a vaccine for protection against superantigen toxin-associated bacterial infections. The vaccine can comprise one or a mixture of individual altered superantigen toxins, or a portion thereof. When a mixture of two or more different altered superantigen toxin from different bacteria is used, the vaccine is referred to as a multivalent bacterial superantigen vaccine. The vaccine is designed to protect against the pathologies resulting from exposure to one or several related staphylococcal and streptococcal toxins. In addition, the protein or polypeptide can be fused or absorbed to other proteins or polypeptides which increase its antigenicity, thereby producing higher titers of neutralizing antibody when used as a vaccine. Examples of such proteins or polypeptides include any adjuvants or carriers safe for human use, such as aluminum hydroxide.

The staphylococcal enterotoxin (SE) serotypes SEA, SED, and SEE are closely related by amino acid sequence, while SEB, SEC1, SEC2, SEC3, and the streptococcal pyrogenic exotoxins B share key amino acid residues with the other toxins, but exhibit only weak sequence homology overall. However, there are considerable similarities in the known three-dimensional structures of SEA, SEB, SEC1, SEC3, and TSST-1. Because of this structural similarity, it is likely that polyclonal antibodies obtained from mice immunized with each SE or TSST-1 exhibit a low to high degree of cross-reaction. In the mouse, these antibody cross-reactions are sufficient to neutralize the toxicity of most other SE/TSST-1, depending upon the challenge dose. For example, immunization with a mixture of SEA, SEB, TSST-1 and SPEa was sufficient to provide antibody protection from a challenge with any of the component toxins, singly or in combination.

The likelihood of substantial antigen-cross-reactivity suggests that it may be possible to obtain immune protection for other (or perhaps all) staphylococcal superantigens by use of a minimal mixed composition of vaccines. For the case of staphylococcal superantigens, a combination of the component vaccines from SEA, SEB, SEC-1 and TSST-1 should be sufficient to provide immune protection against SEA, SEB, SEC1-3, and TSST-1. The addition of SPEa component to the trivalent mixture will allow for sufficient protection against the streptococcal toxins SPEa and SPEc. Therefore, a multivalent vaccine consisting of the altered superantigen toxins from SEA, SEB, SEC-1, TSST-1, and SPEa as described above, is predicted to provide protective immunity against the majority of bacterial superantigen toxins.

The vaccine can be prepared by inducing expression of a recombinant expression vector comprising the gene for the altered toxin described above. The purified solution is prepared for administration to mammals by methods known in the art, which can include filtering to sterilize the solution, diluting the solution, adding an adjuvant and stabilizing the solution. The vaccine can be lyophilized to produce a vaccine against superantigen toxin-associated bacteria in a dried form for ease in transportation and storage. Further, the vaccine may be prepared in the form of a mixed vaccine which contains the altered superantigen toxin(s) described above and at least one other antigen as long as the added antigen does not interfere with the effectiveness of the vaccine and the side effects and adverse reactions, if any, are not increased additively or synergistically. Furthermore, the vaccine may be administered by a bacterial delivery system and displayed by a recombinant host cell such as *Salmonella* spp, *Shigella* spp, *Streptococcus* spp. Methods for introducing recombinant vectors into host cells and introducing host cells as a DNA delivery system are known in the art [Harokopakis et al. (1997) *Infect. Immun.* 65, 1445-1454; Anderson et al. (1996) *Vaccine* 14, 1384-1390; Medaglini et al. (1995) *Proc. Natl. Acad. Sci. U.S.A.* 92, 6868-6872].

The vaccine may be stored in a sealed vial, ampule or the like. The present vaccine can generally be administered in the form of a liquid or suspension. In the case where the vaccine is in a dried form, the vaccine is dissolved or suspended in sterilized distilled water before administration. Generally, the vaccine may be administered orally, subcutaneously, intradermally or intramuscularly but preferably intranasally in a dose effective for the production of neutralizing antibody and protection from infection or disease.

In another embodiment, the present invention relates to a method of reducing superantigen-associated bacterial infection symptoms in a patient by administering to said patient an effective amount of anti-altered superantigen toxin antibodies, as described above. When providing a patient with anti-superantigen toxin antibodies, or agents capable of inhibiting superantigen function to a recipient patient, the dosage of administered agent will vary depending upon such factors as the patient's age, weight, height, sex, general medical condition, previous medical history, etc. In general, it is desirable to provide the recipient with a dosage of the above compounds which is in the range of from about 1 pg/kg to 10 mg/kg (body weight of patient), although a lower or higher dosage may be administered.

In a further embodiment, the present invention relates to a therapeutic method for the treatment of diseases that may not be associated directly with superantigen toxins but which result in specific nonresponsiveness of T-cell subsets or detection of abnormally low level of subsets in peripheral blood, said method comprising the administration of altered superantigen toxins, in vivo or ex vivo, such that T-cell subsets are expanded or stimulated. Diseases which cause anergy or nonresponsiveness of T-cells include, but are not limited to, infectious diseases and cancers. The desired clinical outcome such as an increase in detectable T cell subsets or in stimulation ex vivo of T-cells through their antigen receptors, such as by antigen or anti-CD3 antibody can be measured by standard clinical immunology laboratory assays.

In yet another embodiment, the present invention relates to a therapeutic method for the treatment of diseases associated with expanded or over-stimulated T-cell subsets, such as autoimmunity for example, said method comprising administration in vivo or ex vivo, of superantigen toxin altered in such a manner that only limited (1-3) T-cell subsets are stimulated but that MHC class II binding affinity still remains, such that anergy or inactivation of T-cells is produced. The desired clinical outcome can be measured as a reduction of circulating blood T-cells of the targeted subset(s) or diminished antigen or other antigen receptor-mediated-stimulatory responses by assays known in the art.

Described below are examples of the present invention which are provided only for illustrative purposes, and not to limit the scope of the present invention. In light of the present disclosure, numerous embodiments within the scope of the claims will be apparent to those of ordinary skill in the art.

The following Materials and Methods were used in the Examples that follow.

Structural Comparisons

Primary protein structure data are available for several bacterial superantigens, including SEA, SED, SEB, SEC1-3, TSST-1. Superantigens for which structures were unavailable were modeled using comparative techniques (HOMOLOGY program; Biosym Technologies, Inc., San Diego, Calif.). Before x-ray crystallography data was available, SEA was modeled by using this method, and the model was in very close agreement with the experimentally determined structure. As an example, the amino acid sequence for SEA was aligned with the known structure of free and HLA-DR1 bound SEB, and the SEA molecule was built for both free and DR1-bound proteins. Loop segments of SEA were generated by a de novo method. Refinement of the modeled structures was carried out by means of molecular-dynamics simulations (DISCOVER, Biosym). The constructed free SEA molecule was immersed in a 5-Å layer of solvent water and the α-carbon atoms lying in the structurally conserved regions were tethered to their initial positions during the simulations. For the bound SEA molecule, simulations were carried out by constructing an active-site region composed of part of the SEA molecule and the DR1 molecule inside a 10-Å interface boundary, as derived from the crystal structure of the DR1-SEB complex. Amino acid residues lying in the outer boundary were rigidly restrained at their initial positions. The active-site region was immersed in a 5-Å layer of water. Protein interactions were modeled by employing the consistent valence force field with a non-bonded cutoff distance of 11.0 Å. Simulations were initiated with 100 cycles of minimization using a steepest descent algorithm followed by 100-ps relaxation (using a 1.0 fs timestep). Structural comparisons between SEB, SEC1, and TSST-1 were performed by using the crystal structures (Brookhaven data holdings) aligned according to common secondary structural elements and/or by sequence and structural homology modeling.

Site-Specific Mutagenesis

Site-specific mutagenesis was performed according to the method developed by Kunkel, using gene templates isolated from Staphylococcus aureus strains expressing SEA (FDA196E, a clinical isolate, Fraser, J. D. (1994) Nature 368: 711-718), SEB (14458, clinical isolate), SEC1 (Toxin Technologies, Sarasota, Fla.), TSST-1 (pRN6550 cloned product, a clinical isolate, Kreiswirth, B. N. et al. (1987) Mol. Gen. Genet. 208, 84-87), and SPEa (Toxin Technologies), respectively. Modified T7 polymerase (Sequenase, U.S. Biochemical Corp., Cleveland, Ohio) was used to synthesize second-strand DNA from synthetic oligonucleotides harboring the altered codon and single-stranded, uracil-enriched M13 templates. Mutagenized DNA was selected by transforming E. coli strain JM101. Alternatively, double stranded DNA was used as template for mutagenesis. Mutagenized sequences were confirmed by DNA sequencing (Sanger et al., 1977, Proc. Natl. Acad. Sci. USA 74: 5463-5467; Sambrook et al., 1989) using synthetic primers derived from known sequences, or universal primers. The complete coding sequences were inserted into expression plasmids such as pUC19, pSE380 or pET21 for production in E. coli hosts.

Protein Purifications

The appropriate E. coli hosts were transformed with plasmids harboring the mutant toxin genes, such as pETA489270C (having accession number ATCC 98449, deposited at the American Tissue Culture Collection (ATCC), Manassas, Va. under the terms of the Budapest Treaty on Jun. 4, 1997), pETB2360210 (having accession number ATCC 98447, deposited at the ATCC under the terms of the Budapest Treaty on Jun. 4, 1997), pETB899445P (having accession number ATCC 98446, deposited at the ATCC under the terms of the Budapest Treaty on Jun. 4, 1997), and pETB899445C (having accession number ATCC 98445, deposited at the ATCC under the terms of the Budapest Treaty on Jun. 4, 1997). In general, the bacteria were grown to an A600 0.5-0.6 in Terrific Broth (Difco Laboratories, Detroit, Mich.) containing 50 μg/mL ampicillin or kanamycin. Recombinant proteins were induced with isopropyl-β-D-thio-galactopyranoside (Life Technologies, Gaithersburg, Md.) and recovered as cytoplasmic or bacterial periplasmic secretion products. Bacteria were collected by centrifugation, washed with 30 mM NaCl, 10 mM TRIS (pH 7.6), and pelleted by centrifugation and either lysed or osmotically shocked for collection of secreted proteins. Preparations were isolated by CM Sepharose ion-exchange chromatography, rabbit antibody (Toxin Technologies, Sarasota, Fla.) affinity columns, ion exchange HPLC or similar methods. In some cases partially purified superantigen was further purified by preparative isoelectric focusing (MinipHor; Rainin Instrument Company, Inc., Woburn, Mass.). The MinipHor was loaded with the SEA-enriched fraction from CM Sepharose chromatography in a solution containing 10% (v/v) glycerol and 1% (v/v) pH 6-8 ampholytes (Protein Technologies, Inc., Tucson, Ariz.). The protein preparations were allowed to focus until equilibrium was reached (approximately 4 hr, 40° C.). Twenty focused fractions were collected and aliquots of each were analyzed by SDS-polyacrylamide gel electrophoresis (SDS-PAGE) and immunoblotting. The SEA-containing fractions were pooled, and refocused for an additional 4 h. The fractions containing purified SEA were pooled and dialyzed first against 1 M NaCl (48 h, 40° C.) to remove ampholytes, and then against PBS (12 h, 40° C.). Legitimate amino-terminal residues were confirmed by protein sequencing. Precise measurements of protein concentrations were performed by immunoassay using rabbit antibody affinity-purified with the wild-type superantigens and by the bicinchoninic acid method (Pierce, Rockford, Ill.) using wild-type protein as standards. All protein preparations were >99% pure, as judged by SDS-PAGE and Western immunoblots. In some cases, as when used for lymphocyte assays, bacterial pyrogens were removed by passing the protein preparations over Polymyxin B affinity columns.

Binding of Superantigens to HLA-DR1

The DR1 homozygous, human B-lymphoblastoid cell line LG2 or L cells transfected with plasmids encoding HLA-DR1αβ were used in the binding experiments. Cells were incubated 40 min (37° C.) with wild-type or mutant superantigen in Hanks balanced salt solution (HBSS) containing 0.5% bovine serum albumin. The cells were washed with HBSS and then incubated with 5 µg of specific rabbit antibody (Toxin Technology, Sarasota, Fla.) for 1 h on ice. Unbound antibody was removed, and the cells were incubated with FITC-labelled goat anti-rabbit IgG (Organon Teknika Corp., Durham, N.C.) on ice for 30 min. The cells were washed and analyzed by flow cytometry (FACScan; Becton Dikinson & Co., Mountain View, Calif.). Controls consisted of cells incubated with affinity purified anti-toxin and the FITC labelled antibody without prior addition of superantigen.

Lymphocyte Proliferation

Human peripheral blood mononuclear cells were purified by Ficoll-hypaque (Sigma, St. Louis, Mo.) buoyant density gradient centrifugation. Genes encoding the human MHC class II molecules DR1αβ (DRA and DRB1*0101 cDNA [Bavari and Ulrich (1995) Infect. Immun. 63, 423-429] were cloned into the eukaryotic expression vector pRC/RSV (Invitrogen, Carlsbad, Calif.), and mouse L cells were stably transfected. The transfectants were selected by fluorescence-activated cell sorting (EPICS C, Coulter Corp., Hialeah, Fla.) using rabbit anti-DRαβ antisera and FITC-goat anti-rabbit IgG, to produce cells that expressed a high level of DRαβ21. $1 \times 10^5$ cells/well of a 96-well plate were irradiated (15,000 Rad), and wild-type or mutant SE, was added. After a brief incubation period (45 min, 37° C.), unbound SE was rinsed from the culture plates using warm media. The cells were cultured in RPMI-1640 (USAMRIID) with 5% FBS for 72 h, and pulsed-labelled for 12 h with 1 µCi [$^3$H]-thymidine (Amersham, Arlington Heights, Ill.). Cells were harvested onto glass fiber filters, and [$^3$H]-thymidine incorporation into the cellular DNA was measured by a liquid scintillation counter (BetaPlate, Wallac Inc., Gaithersburg, Md.). Splenic mononuclear cells or human peripheral blood mononuclear cells were obtained by buoyant density centrifugation (Histopaque; Sigma Chemical Comp.) and washed three times. The cells were resuspended in medium containing 5% fetal bovine serum (FBS), and 100 µl ($4 \times 10^5$ cells) of the cell suspension was added to triplicate wells of 96-well flat bottom plates. The mononuclear cells were cultured (37° C., 5% $CO_2$) with WT or mutant SEA. After 3 days the cultures were pulsed (12 h) with 1 µCi/well of [$^3$H]thymidine (Amersham, Arlington Heights, Ill.) and incorporated radioactivity was measured by liquid scintillation.

Gel Electrophoresis and Immunoblotting Analysis.

The protein preparations were analyzed by SDS-PAGE (12%) and stained with Coomassie Brilliant Blue R-250 (Sigma Chemical Comp. St Louis, Mo.) in methanol (10% v/v) acetic acid (10% v/v). The proteins separated by SDS-PAGE (not stained) were transferred to nitrocellulose membranes (Bio-Rad Lab. Inc., Melville, N.Y.) by electroblotting, and the membranes were then blocked (12 h, 4° C.) with 0.2% casein in a buffer consisting of 50 mM sodium phosphate, 140 mM sodium chloride, pH 7.4 (PBS). The membrane was then incubated (1 h, 37° C., shaking) with 2 µg/mL of affinity-purified anti-toxin antibody (Toxin Technology, Sarasota, Fla.) in PBS with 0.02% casein. After the membranes were thoroughly washed, peroxidase-conjugated goat anti-rabbit IgG (Cappel/Organon Teknika Corp., West Chester, Pa.) was added (1:5,000) and the membranes were incubated for 1 h (37° C.) with shaking. The unbound antibody was removed by washing with PBS and bound antibody was visualized by using a Bio-Rad peroxidase development kit (Biorad, Hercules, Calif.). For quantitation, dilutions of wild-type preparations were immobilized on nitrocellulose membranes by using a Slot-Blot apparatus (Bio-Rad). The membrane was removed from the Slot-Blot apparatus and unreacted sites were blocked (12 h, 4° C.) with 0.2% casein in PBS. After washing once with the PBS, the membrane was incubated (1 h, 37° C.) with 2 µg/mL rabbit affinity purified anti-toxin antibody (Toxin Technology) in PBS that contained 0.02% casein. After four washes, the bound rabbit antibody was reacted with goat anti-rabbit IgG conjugated with horseradish peroxidase (1 h, 37° C.) and the blots were developed using enhanced chemiluminescence (ECL; Amersham Life Sciences, Arlington Heights, Ill.) or similar methods. The amount of mutant protein was measured by densitometry (NIH Image 1.57 software, National Institutes of Health, Bethesda, Md.) of exposed X-ray film. Standard curves were prepared by plotting the mean of duplicate densitometric readings for each dilution of toxin standard. The resulting values were fitted to a straight line by linear regression. Concentrations of proteins were determined by comparing mean values of various dilutions of the mutant to the standard curve.

Biological Activities and Immunizations.

Male C57BL/6 mice, 10 to 12-weeks old, were obtained from Harlan Sprague-Dawley, Inc. (Frederick Cancer Research and Development Center, Frederick, Md.). The lethal effect of WT or mutant SEA was evaluated as described in Stiles et al. (1993) Infect. Immun. 61, 5333-5338. For immunizations, mice were given by interperitoneal (ip) injections either 2 or 10 µg of WT or mutant toxin in 100 µl of adjuvant (RIBI, Immunochem Research, Inc. Hamilton, Mont. or alum), or adjuvant only, and boosted (ip) at 2 and 4 weeks. Serum was collected from tail veins one week after the last immunization. Mice were challenged 2 weeks after the last injection with toxin and lipopolysaccharide (LPS, 150 μg) from *E. coli* 055:B5 serotype (Difco Laboratories, Detroit, Mich.). Challenge controls were adjuvant-immunized or non-immunized mice injected with both agents (100% lethality) or with either wild type toxin or LPS. No lethality was produced by these negative controls. Monkeys were immunized with the antigen in the right leg, caudal thigh muscles. Each received three intramuscular immunizations with a superantigen vaccine plus adjuvant. Control monkeys received 0.5 ml total volume of adjuvant (Alhydrogel, Michigan Department of Public Health) and sterile PBS using the same techniques and equipment as the immunized monkeys. Immunizations were administered 28±2 days apart and consisted of 20 μg of the vaccine in adjuvant in a total volume of 0.5 ml. Immunizations were administered on day 0, 28±2, and 56+2 using a 23-27 ga ½-⅝" needle attached to a 1 ml tuberculin syringe into the caudal thigh.

Antibody Assay.

Microtiter plates were coated with 1 μg/well of WT toxin in 100 μl of PBS (37° C., 2 h). After antigen coating, the wells were blocked with 250 μl of casein 0.2% in PBS for 4 h at 37° C. and then washed four times with PBS containing 0.2% Tween 20. Immune or nonimmune sera were diluted in PBS containing 0.02% casein and 100 μl of each dilution was added to duplicate wells. After each well was washed four times, bound antibody was detected with horse radish peroxidase (Sigma Chemical Comp., St. Louis, Mo.) labelled goat anti-species specific IgG (37° C., 1 h), using O-phenylenediamine as the chromogen. Mean of duplicates OD (absorbance at 490 nm) of each treatment group was obtained and these data were compared on the basis of the inverse of the highest serum dilution that produced an OD reading four times above the negative control wells. For negative controls, antigen or serum was omitted from the wells.

Superantigen Binding and TCR Subset Analysis.

Cells from the mouse B-lymphoma line A20 (ATCC, Rockville, Md.) ($2-4\times10^5$ cells) were incubated (40 min at 37° C.) with WT or mutant toxin in Hanks balanced salt solution containing 0.5% bovine serum albumin (HBSS, USAMRIID). The cells were washed with HBSS and incubated with 5 μg of affinity-purified anti-toxin antibody in HBSS (4° C., 45 min). Unbound antibody was removed and the bound antibody was detected with fluorescein isothiocyanate (FITC)-labelled, goat anti-rabbit IgG (Organon Teknika Corp., Durham, N.C.). Unbound antibody was removed and the cells were analyzed by with a FACSort flow cytometer (Becton Dikinson & Co., Mountain View, Calif.).

For TCR subset analysis, splenic mononuclear cells were obtained from mice immunized with WT or mutant toxin. The mononuclear cells were incubated (37° C.) with WT toxin (100 ng/mL) for 5 days and then cultured in 85% RPMI-1640, 10% interleukin-2 supplement (Advanced Biotechnologies Inc., Columbia, Md.) with 5% FBS for an additional 5 days. The T cells were washed twice and stained with anti-TCR (Biosource, Camarillo, Calif.) or anti-VS specific TCR (Biosource, Camarillo, Calif.) (45 min, 4° C.). All cells analyzed were positive for T cell marker CD3+ and expressed the CD25 activation marker (data not shown). Controls were incubated with an isotype matched antibody of irrelevant specificity. Unreacted antibody was removed, and the cells were incubated with an FITC-labelled, anti-mouse IgG (Organon Teknika Corp, Durham, N.C.) on ice for 30 min. The cells were washed and analyzed by flow cytometry (FACSort).

LPS Potentiation of SE Toxicity in Mice.

C57BL/6 or BALB/c mice weighing 18-20 g (Harlan Sprague Dawley, Inc., Frederick Cancer Research and Development Center, Frederick, Md.) were each injected intraperitoneally (i.p.) with 200 μl of PBS containing varying amounts of SEA, SEB, or SEC1, TSST-1, or SPEa followed 4 h later with 75 or 150 μg of LPS (200 μl/i.p.). Controls were each injected with either SE (30 mg) or LPS (150 mg). Animals were observed for 72 h after the LPS injection. Calculations of LD50 were done by Probit analysis using 95% fiducial limits (SAS Institute Inc., Cary, N.C.).

The biological effects of SEA and SEB were also tested in transgenic C57BL/6 mice (GenPharm International, Mountain View, Calif.) deficient in MHC class I or II expression (Stiles et al. (1993) *Infect. Immun.* 61, 5333-5338], as described above, using a single dose of toxin (30 μg/mouse). Genetic homozygosity was confirmed by Southern analysis of parental tail DNA, using β2 microglobulin and MHC class II β DNA probes.

Detection of Cytokines in Serum.

Mice (n=18 per group) were injected with toxin (10 μg), LPS (150 μg), or toxin plus LPS. Sera were collected and pooled from three mice per group at each time point (2, 4, 6, 8, 10, 22 h) after LPS injection. Sera were collected at various time points following toxin injection (−4 h, or 4 h before LPS injection, for data tabulation). Collection of LPS control sera began at the time of injection (0 h).

Serum levels of TNFα and IL-α were detected by an enzyme linked immunosorbent assay (ELISA). TNFα was first captured by a monoclonal antibody against mouse TNFα (GIBCO-BRL, Grand Island, N.Y.) and then incubated with rabbit anti-mouse TNFa antibody (Genzyme, Boston, Mass.). The ELISA plate was washed and peroxidase conjugate of anti-rabbit antibody (Boehringer Mannheim, Indianapolis, Ind.) added to the wells. After washing the plate and adding substrate (Kirkegaard and Perry, Gaithersburg, Md.), TNFα concentrations were measured using the mean A450 reading of duplicate samples and a standard curve generated from recombinant mouse TNFα (GIBCO-BRL). Serum levels of IL-1α were determined from the mean reading of duplicate samples with an ELISA kit that specifically detects murine IL-1α (Genzyme, Boston, Mass.). The standard error of the mean (SEM) for TNFα and IL-1α readings was +/−5%.

Quantitation of IL-6 and IFNγ were measured by bioassays [See et al. (1990) *Infect. Immun.* 58: 2392-2396]. An IL-6 dependent cell line, 7TD1 (kindly provided by T. Krakauer), was used in a proliferative assay with serial two-fold dilutions of serum samples assayed in triplicate. Proliferation of 7TD1 cells in a microtiter plate was measured by uptake of [$^3$H]-thymidine (1 μCi/well; Amersham, Arlington Heights, Ill.) and the activity of IL-6 from serum was compared to a recombinant mouse IL-6 standard (R and D Systems, Minneapolis, Minn.) as previously described [See et al. (1990) *Infect. Immun.* 58: 2392-2396]. The SEM of triplicate samples was +/−10%.

IFNγ was measured by the reduction of vesicular stomatitis virus (New Jersey strain) cytopathic effects on L929 cells, as previously described [Torre et al. (1993) *J. Infect. Dis.* 167, 762-765]. Briefly, serial two-fold dilutions of serum were made in duplicate and added to microtiter wells containing L929 cells ($5\times10^4$/well). After incubating 24 h, virus ($5\times10^5$ PFU/well) was added and the cytopathic effects measured at 48 h by absorbance readings (570 nm) of reduced 3-[4,5-dimethylthiazol-2-yl]-2,5 diphenyl tetrazolium bromide (Sigma). The activity of each serum sample was determined using recombinant mouse IFNγ as a standard (Biosource, Camarillo, Calif.) The SEM of duplicate samples was +/−5%.

EXAMPLE 1

Molecular modelling and structural studies of staphylococcal and streptococcal superantigens: bacterial superantigens share common 3-dimensional structure.

Comparison of amino acid sequences (FIG. 1) suggested that bacterial superantigens fall into groups consisting of (1) SEA, SED and SEE, (2) SEB, staphylococcal enterotoxins $C_1$-$C_3$ (SEC1-3), the streptococcal pyrogenic exotoxins A (SPE-A) and C (SPE-C), (3) TSST-1 and (4) the exfoliative toxins (ETA, ETB) and streptococcal pyrogenic exotoxin B (SPE-B), which are the most distant from the others in sequence. Although not available to the inventor when the inventions were first conceived and proof of principle was obtained, the x-ray crystallographic structures of several bacterial superantigens are now known. Diverse superantigens, such as SEB and TSST-1, appear to have little sequence in common, yet they exhibit homologous protein folds composed largely of β strands [Prasad, G. S. et al. (1993) *Biochemistry* 32, 13761-13766; Acharya, R. K. et al. (1994) *Nature* 367, 94-97; Swaminathan, S. et al. (1992) *Nature* 359, 801-806]within two distinct domains. Differences between the proteins are located primarily in highly variable regions comprised of several surface loops, such as the disulfide-bonded loop which is absent from TSST-1 and at the amino terminus.

The X-ray crystal structures of SEB and TSST-1 complexed with HLA DR1 are known [Kim, J. et al. (1994) *Science* 266, 1870-1874; Jardetzky, T. S. et al. (1994) *Nature* 368, 711-718] and this data was useful to fully explain our results concerning attenuation of the superantigens by site-specific mutagenesis. The region of HLA DR1 that contacts SEB consists exclusively of α subunit surfaces. The main regions of SEB involved are two conserved sites: a polar pocket derived from three β strands of the β barrel domain and a highly solvent-exposed hydrophobic reverse turn. The polar binding pocket of SEB contains a glutamate and two tyrosines that accommodate Lys39 of the α subunit of HLA DR1, while the hydrophobic region consists of a leucine and flanking residues that make several contacts with the HLA DRα chain. The HLA DR1 binding sites of both TSST-1 and SEB overlap significantly. The hydrophobic binding contacts of other SAg with the HLA DRα chain have been proposed [Ulrich et al. (1995) *Nature, Struct. Biol.* 2, 554-560]to be similar to those found in SEB and TSST-1. A motif consisting of a leucine in a reverse turn [Ulrich et al. (1995), supra] is conserved among bacterial superantigens and may provide the key determinant (hydrophobic or otherwise) for binding HLA-DR. However, TSST-1 does not have a highly charged residue in the polar pocket that interacts with Lys39 of the HLA DRα chain and uses an alternative conformational binding mode that allows TSST-1 to interact with HLA DR1 β-chain residues and the carboxy-terminal region of the antigenic peptide.

Both SEA and SEE bind to the β subunit of DR by means of a single zinc atom [Fraser, J. D. et al. (1992) *Proc. Natl. Acad. Sci. USA* 89, 5507-5511]. The amino-terminal domain of SEA interfaces with the HLA DRα chain [Ulrich et al. (1995), supra], while SEA C-terminal domain residues His187, His225 and Asp227 form a zinc-coordination complex, likely with His-81 from the β chain of an adjoining HLA DR molecule. However, our results have shown that binding of superantigen to the HLA DRβ subunit does not directly stimulate T cells (Ulrich et al. (1995), supra] but increases the potential of the bound SEA to interact with the α chain of another HLA DR, thus increasing the biological potency.

EXAMPLE 2

Molecular modelling and structural studies of staphylococcal and streptococcal superantigens: A detailed protein structure analysis of SEB and SEA suggested that all bacterial superantigens have a common mechanism for binding MHC class II receptors.

A least-squares superimposition of the unbound molecules of modeled SEA and the crystal structure of SEB, aligned according to their structurally conserved α-helical and β-strand regions, exhibited a global folding pattern which is very similar. Differences between the two structures are calculated to be located primarily in loops of low sequence homologies, with the largest positional deviations occurring between structurally conserved regions of residues 18-20, 30-32, 173-181, 191-194, and the cysteine-loop region (90-111). Only one of these regions in SEB makes significant contact (residue Y94 in particular) with the HLA-DR1 molecule [Jardetzky, T. S. et al. (1994) *Nature* 368, 711-718].

The binding interface between SEB and HLA-DR1 consists principally of two structurally conserved surfaces located in the N-terminal domain: a polar binding pocket derived from three β-strand elements of the β-barrel domain and a hydrophobic reverse turn. The binding pocket of SEB contains residues E67, Y89 and Y115, and binds K39 of the DRα subunit. For SEA, the binding interface with the DR molecule is modeled to contain a similar binding pocket consisting of residues D70, Y92 and Y108. Mutation of residue Y89 in SEB or Y92 in SEA to alanine (FIG. 2) resulted in 100-fold reduction in DR1 binding. The substitution of alanine for Y89 in SEB and Y92 in SEA eliminates the hydrogen bond with K39 and disrupts packing interactions with adjacent protein residues. Modeling of the SEA mutant Y92A predicts an increase in solvent-accessible surface area for Y108 by a factor of two greater than the wild-type structure, allowing the formation of a hydrogen bond to the carboxylate group of D70 and thus disrupting key anchoring and recognition points for HLA-DR1. This effect is expected to be somewhat less in SEB due to the longer side chain at E67. Substitution of SEB Y115 with alanine also resulted in 100-fold reduction of binding. In contrast, the same replacement of Y108 in SEA yielded little to no change in DR1 binding (FIG. 2*a*), suggesting the primary importance of SEA residues Y92 and D70 for stabilizing interactions with K39. The K39 side chain of DRα forms a strong ion-pair interaction with the SEB E67 carboxylate group and hydrogen bonds with the hydroxyl groups of Y89 and Y115. Substitution of SEB E67 by glutamine reduced binding affinity by 100-fold (FIG. 2), reflecting the replacement of the strong ionic bond with a weaker hydrogen bond. To optimize ion-pair interactions of the analogous SEA site, the shorter carboxylate side chain of D70 is predicted to shift K39 of DRα, weakening interactions with SEA Y10B. The substitution of alanine for SEA Y108 is thus more easily accommodated than the homologous substitution of SEB Y115, without loss in DR1 binding.

Comparisons of the polar pocket with other bacterial superantigens were then made. SEC1-3 and SPE-A have conserved the critical DR1 binding-interface residues (FIG. 1), and share with SEB and SEA secondary structural elements of the DR1-binding surfaces. Asparagine in SED (N70) replaces the acidic side chain present in SEA, SEB, SPE-A and SEC1-3. Accordingly, for SED the salt bridge of the polar pocket is likely to be replaced by a hydrogen bond. Overall DR1 affinities for SED and SEA appeared to be equivalent (FIG. 2*b*), indicating that other interactions may compensate for the absence in SED of the ion-pair found in the other superantigens. For the case of TSST-1, mutating DRα residues K39 to serine or M36 to isoleucine has been shown to greatly reduce binding [Panina-Bordignon et al. (1992) *J. Exp. Med.* 176: 1779-1784]. Although primarily hydrophobic, the critical TSST-1 structural elements are conserved with the SEA and SEB polar binding pocket. SEB residues Y89 and Y115 are homologous to T69 and I85 in TSST-1, respectively, and SEB E67 is replaced by I46. These TSST-1 residues are positioned in a conserved β-barrel domain found in both SEB and SEA. However, the TSST-1 site lacks polarity equivalent to SEB/SEA, and hydrogen bonding with the hydroxyl of TSST-1 residue T69 would require that DRα K39 extend 5 Å into the pocket. TSST-1 binding utilizes an alternative strategy [Kim et al. (1994) *Science* 266: 1870-1874] consisting of hydrophobic contacts centered around residue I46, and potential ionic or hydrogen bonds bridging DRα residues E71 and K67 to R34 and D27, respectively, of TSST-1.

The hydrophobic region of the binding interface between SEB and the HLA-DR1 molecule consists of SEB residues 44-47, located in a large reverse turn connecting β-strands 1 and 2 of SEB. These residues appear to make strong electrostatic interactions with DRα through their backbone atoms. The mutation of L45 to an arginine reduced overall HLA-DR1 binding greater than 100-fold (FIG. 2b), attributable to the less energetically favorable insertion of a highly charged residue into a hydrophobic depression on the DR1 molecule. The modeled DR1-SEA. complex presents similar interactions with the SEA backbone atoms, with the exception of a glutamine (Q49) replacing SEB Y46. Mutation of L48 to glycine in SEA (homologous to L45 of SEB) has been reported to decrease T-cell responses. SEB L45 and the comparable L30 of TSST-1 are the most extensively buried residues in the DR1 interface. The leucine is conserved among the bacterial superantigens (FIG. 3) and may provide the necessary hydrophobic structural element for surface complementarity with DR1, consistent with the mutagenesis data for SEB and SEA.

The inventor has performed similar structure and function studies with TSST-1, SEC1 and SPE-A.

EXAMPLE 3

Molecular modelling and structural studies of staphylococcal and streptococcal superantigens: Some interactions of bacterial superantigens with MHC class II receptors are not conserved but are less important than the hydrophobic loop and polar pocket binding sites.

In determining the overall affinity of the superantigen for DR1, a contributory role is played by structural variations around the common binding motifs. A short, variable structured, disulfide-bonded loop is found in SEA and a homologous longer loop in SEB. The SEB residue Y94, contained within this loop, forms hydrophobic interactions with L60 and A61 of the DRα subunit. Replacement of Y94 with alanine partially inhibits DR1 binding (FIG. 2a, b). An alanine is found in SEA (A97) and SEE at the position equivalent to SEB Y94, and mutating this residue in SEA to tyrosine results in disrupted instead of stabilized interactions with DR1 (FIG. 2a). Although the disulfide loops differ in structure between SEA and SEB, A97 apparently contributes to the DRα binding interface in a manner similar to Y94 of SEB. Because TSST-1 lacks a disulfide loop, similar contacts with DRα are replaced by interactions with β-strands of TSST-1. In a like manner, the absence of a salt bridge between the residues K39 of DRα and E67 of SED is apparently compensated for by stabilizing interactions occurring outside of the otherwise conserved dominant binding surfaces (FIG. 2a).

EXAMPLE 4

Molecular modelling and structural studies of staphylococcal and streptococcal superantigens: Superantigen interactions with T-cell antigen receptors.

The amino acid residues in contact with TCR are located in regions of high sequence variability, presenting a unique surface for interaction with the TCR. Residues implicated in TCR interactions by mutagenesis of SEA and SEB reside in variable loop regions, while TSST-1 mutants that affect TCR binding are mainly located in an α helix [Acharya, R. K. et al. (1994) *Nature* 367, 94-97; Kim, J. et al. (1994) *Science* 266, 1870-1874]. Specifically, mutations that diminish T-cell receptor recognition of SEB include residues N23, Y61, and the homologous SEA N25 or Y64 (FIG. 2c). SEA residues S206 and N2O7 also control T-cell responses [Hudson, et al. (1992) *J. Exp. Med.* 177: 175-184]. Mutants of the polar binding pocket, SEA Y92A and SEB Y89A, equivalently reduced T-cell responses (FIG. 2c), reflecting the observed decreases in DR1-binding (FIG. 2a, b). While supporting reduced T-cell responses, mutants SEA Y64A and SEB Y61A retained normal affinities for DR1 (FIG. 2a-c).

EXAMPLE 5

Animal models for determining biological activity of bacterial superantigens: Mouse.

When compared to primates, mice are not very susceptible to the toxic effects of SE, and we therefore sought to increase sensitivity with a potentiating dose of lipopolysaccharide (LPS) from Gram-negative bacteria [Stiles et al. (1993) *Infect. Immun.* 61, 5333-5338]. There was no apparent effect in control animals injected with any of the SE (up to 30 μg/mouse) or LPS (150 μg/mouse) alone (Table 1). Incremental injections of LPS were also not lethal, when given in amounts up to 250 μg/mouse (data not shown). However, mice died between 24-48 h after SE and LPS were given to the same animal (Table 1). SEA was much more toxic than either SEB or SEC1 and the calculated LD50 (μg toxin/kg) of SEA, SEB, and SEC1 with 95% fiducial limits was 18.5 (6.5, 38.5), 789.0 (582.5, 1044.5), and 369.0 (197.5, 676.0), respectively.

TABLE 1

Titration of SEA, SEB, and $SEC_1$ in the C57BL/6 mouse lethality assay

| | % Lethality (no. of mice tested) with the following dose of SE, in micrograms/mouse[b]: | | | |
|---|---|---|---|---|
| Stimulus[a] | 30 | 10 | 1 | 0.1 |
| SEA + LPS | 93 (15)[b] | 85 (20) | 80 (15) | 20 (10) |
| SEB + LPS | 80 (15) | 27 (15) | 0 (15) | 0 (15) |
| $SEC_1$ + LPS | 80 (10) | 60 (10) | 10 (10) | 0 (10) |

[a]LPS was injected into each mouse (150 ug) 4 h after the SE injection. Control mice injected with 150 ug of LPS (n = 20) or 30 ug of SEA, SEB, or SEC1 (n = 10) survived.

[b]Results are from a combination of separate experiments with five mice per experiment.

The role of MHC class I and class II molecules in SE toxicity, potentiated by LPS, was addressed by using transgenic, MHC-deficient mice (Table 2). Class II-deficient animals were unaffected by a dose of SE (30 μg) plus LPS (150 μg) that was lethal for 93% of wild-type and 30% of class I-deficient mice. Mononuclear cells from class II-deficient animals were not able to present SEA, as measured by proliferative responses. MHC class I-deficient cells were functional in supporting T-cell proliferation, but at levels <30% of the proliferative response supported by MHC-wild-type presenting cells (Table 3). Cell surface expression levels were normal, when compared to nontransgenic C57BL/6, for $A^b$ in class I-deficient mice, and $K^b/D^b$ in class II-deficient mice. The T-cell responses of MHC class I- or class II-deficient mice were essentially equivalent to wild-type when SEA was presented by mononuclear cells expressing both class I and II molecules (Table 3).

TABLE 2

Lethality of SEA and SEB in C57BL/6 mice lacking MHC class I or class II

| Stimulus[a] | % Lethality (no. of mice tested) with the following MHC class phenotype | | |
|---|---|---|---|
| | I⁻II⁺ | I⁺II⁻ | I⁺II⁺ |
| SEA + LPS | 30 (10) | 0 (5) | 93 (15) |
| SEA + LPS | ND[b] | 0 (5) | 80 (15) |
| SEA only | 0 (2) | 0 (2) | 0 (2) |
| SEB only | ND[b] | 0 (2) | 0 (2) |
| LPS only | 0 (5) | 0 (5) | 0 (5) |

[a]Mice were injected with 30 ug of SEA or SEB and, 4 h later, with 150 ug of LPS, as indicated. Control mice were injected with only SEA, SEB, or LPS.
[b]ND, not determined.

TABLE 3

Mouse T-cell responses to SEA are MHC class II-dependent

| T-cell/APC source[3] | T-cell responses[1] | |
|---|---|---|
| | 0.1 µg/ml SEA | 1 µg/ml SEA |
| Wild-type C57/BL6 mouse/autologous | 430,000 cpm[2] | 700,000 cpm |
| MHC class I knock-out C57/BL6 mouse/autologous | 117,000 cpm | 167,000 cpm |
| MHC class II knock-out C57/BL6 mouse/autologous | 8,000 cpm | 33,000 cpm |
| Wild-type C57/BL6 mouse/wild-type | 305,000 cpm | 307,000 cpm |
| MHC class I knock-out C57/BL6 mouse/wild-type | 420,000 cpm | 445,000 cpm |
| MHC class II knock-out C57/BL6 mouse/wild-type | 310,000 cpm | 322,000 cpm |

[1]Cultures of mononuclear cells derived from mouse spleens, cultured for 3 d with the indicated amount of SEA.
[2]Data represent the mean of triplicate determinations (<10 SEM) of [³H] thymidine incorporation.
[3]Antigen presenting cells (APC) were isolated from spleens of the indicated mouse strain and added to cultures.

The serum levels of TNFα, IL-1α, IL-6, and IFNγ in mice injected with SEA, LPS, or SEA plus LPS were measured at various times following injection (FIG. 4). Compared to mice injected with either SEA or LPS alone, the serum levels of TNFα, IL-6, and IFNγ had increased 5-, 10-, and 15-fold, respectively, in animals given SEA plus LPS. SEA alone did not elicit any detectable increase of TNFα, IL-6, or IFNγ above background. In contrast to the other cytokines, IL-1α levels in mice injected with SEA plus LPS resulted in a simple additive effect.

Serum levels of TNFα, IL-6, and IFNγ were maximal 2-4 h after the LPS injection, but returned to normal by 10 h. The concentration of IL-1α in mice given SEA plus LPS had also peaked 2 h after the LPS injection, but stayed above background for the remaining determinations. Levels of IL-1α in mice given only LPS or SEA peaked at 4 and 6 h, respectively. Unlike profiles for other cytokines, the highest amount of IL-1α in mice injected with SEA and LPS corresponded to the peak stimulated by SEA, but not LPS.

This animal model was used in various stages of developing the inventions, as a means of assessing the physiological activity of mutated superantigens. Control animals survived the maximum dose of either SE or LPS, while mice receiving both agents died. Wild-type SEA was 43-fold more potent than SEB and 20-fold more potent than SEC1. By using BALB/c mice the toxicity of SEB was 10-20 fold higher. These data confirmed that the toxicity of SE was mainly exerted through a mechanism dependent on expression of MHC class II molecules and was linked to stimulated cytokine release. Thus this was a relevant preclinical model that could be used to predict human responses.

EXAMPLE 6

Animal models for determining biological activity of bacterial superantigens: Rhesus monkey The physiological responses of the rhesus monkey to bacterial superantigens is probably identical to humans, with the exception of sensitivity [Bavari and Ulrich (1995) *Clin. Immunol. Immunopath.* 76:248]. Generally SEB intoxicated monkeys developed gastrointestinal signs within 24 hours post-exposure. Clinical signs were mastication, anorexia, emesis and diarrhea. Following mild, brief, self-limiting gastrointestinal signs, monkeys had a variable period of up to 40 hours of clinical improvement. At approximately 48 hours post-exposure, intoxicated monkeys generally had an abrupt onset of rapidly progressive lethargy, dyspnea, and facial pallor. If given a lethal dose, death occurs within four hours of onset of symptoms. Only SEB has been used in challenges of rhesus monkeys to determine physiological/pathological effects. Human responses to bacterial superantigens are characterized by a rapid drop in blood pressure, elevated temperature, and multiple organ failure-the classical toxic shock syndrome (TSS). However, the respiratory route of exposure may involve some unique mechanisms. The profound hypotension characteristic of TSS is not observed, and respiratory involvement is rapid, unlike TSS. Fever, prominent after aerosol exposure, is generally not observed in cases of SEB ingestion.

EXAMPLE 7

Targeting receptor interactions to develop vaccines.

The SEA mutants Y92A, with reduced DR1 binding, and Y64A, with reduced TCR interactions, and K14E with wild-type (control) activity were used to determine the correct receptor to target for vaccine development. The binding of WT or mutant SEA was evaluated with the MHC class II expressing murine B-cell lymphoma cell line A20 (Table 4). The binding affinity of WT SEA to mouse MHC class II (H-2d) molecules was lower than that observed with human MHC class II expressing cells, reflecting the reduced toxicity that bacterial SAgs exert in mice. WT SEA, Y64A and K14E all had the same relative affinity to mouse MHC class II molecules. Similar to the results obtained with human MHC class II molecules, the Y92A mutant exhibited substantially reduced binding to A20 cells (Table 4).

TABLE 4

Biological activity of superantigen vaccines

| toxin | T-cell anergy[1] | MHC classII binding[2] | T-cell response |
|---|---|---|---|
| SEA wild type | ++++ | +++ | +++ |
| TCR attenuated Y64A | + | +++ | +/− |

TABLE 4-continued

Biological activity of superantigen vaccines

| toxin | T-cell anergy[1] | MHC classII binding[2] | T-cell response |
|---|---|---|---|
| MHC attenuated Y92A | − | +/− | +/− |
| Control K14E | ++++ | +++ | +++ |

[1]Based on attenuation of T-cell response to wild-type SEA in mice immunized with the mutant or wild-type SEA.
[2]Binding to the mouse MHC class II+ A20 cells, measured by flow cytometry The effect of WT SEA or site-specific SEA mutants on splenic mononuclear cells obtained from nonimmunized C57BL/6 (H-2b) mice is summarized in Table 4. Both WT SEA and the control mutant K14E were potent T cell activators, effective at minimal concentrations of 10 to 100 pg/mL. However, T-cell responses to Y92A were reduced at least 100-fold, compared to SEA wild type, while Y64A-stimulated responses were slightly higher than Y92A. These results confirmed that attenuation of superantigen binding to either MHC class II or TCR molecules resulted in dramatically reduced mouse T-cell proliferation. These results may indicate that the altered toxin may compete with wild type toxin for TCR binding.

SEA WT (10 LD50), site-specific SEA mutants (10 μg/mouse each) or LPS (150 μg/mice) injected alone were nonlethal to mice (Table 5). However, combining LPS with either WT SEA or mutant K14E resulted in 100% lethality. For those mice receiving both LPS and WT or K14E SEA, 80% were dead by 24 h and 100% by 48 h. In contrast, 100% of Y92A and 80% of Y64A injected mice (coadministered with LPS) survived. The average time to death for the 20% of mice that did not survive Y64A injection occurred at 48 to 72 h. These in vivo data correlated well with the results obtained with the lymphocyte cultures. It was concluded that the observed attenuation of toxicity in mice was a direct result of the reduced T-cell proliferation.

TABLE 5

Biologic effect of wild type (WT) staphylococcal enterotoxin A (SEA) and SEA mutants.

| Protein | No. live/total |
|---|---|
| WT | 0/10 |
| K14E | 0/10 |
| Y64A | 8/10 |
| Y92A | 10/10 |

NOTE.
Mice were given 10 LD$_{50}$ (10 ug) of WT or mutant SEA.
Lipopolysaccharide (150 ug/mouse) was injected 3 h later.

Having established that attenuation of receptor binding resulted in reduced toxicity, we next examined the immunogenicity of the SEA mutants. Mice were immunized with WT or mutant SEA. Control mice received adjuvant only or were left untreated. One week before challenge with WT SEA, mice were bled and serum antibody titers were determined for each group (Table 6). Mice immunized with the 2 μg of Y64A or Y92A had serum antibody titers of 1:5000 and 1:1000, respectively. Immunization with 2 μg of WT SEA or control mutant resulted in titers of 1:5,000 and 1:10,000, respectively. The highest immunizing dose (10 μg/mouse) was most effective for all animals, resulting in antibody titers which were greater than 1:10,000. All mice were challenged with 10 LD50 of WT SEA (potentiated with LPS). The survival data correlated well with the levels of serum antibodies in immunized mice. All mice that were vaccinated with 10 μg of Y64A or Y92A, survived the lethal challenge dose of WT SEA. Slightly less protection was afforded by the lower vaccination dose of mutant Y64A or Y92A. All mice immunized with both doses of WT SEA survived the lethal challenge with WT potentiated with LPS. Mice immunized with mutant K14E exhibited survivals of 100% and 80% for high and low vaccination doses, respectively. All nonimmunized or control mice that were vaccinated with adjuvant alone died when challenged with WT SEA and a potentiating dose of LPS.

TABLE 6

Mice immunized with attenuated forms of staphylococcal enterotoxin A (SEA) produce high titers of neutralizing antibody.

| Immunizing agent | Dose (ug/mouse) | Anti-SEA antibody titer* | No. live/total |
|---|---|---|---|
| WT | 2 | 10,000-50,000 | 10/10 |
|  | 10 | 10,000-50,000 | 10/10 |
| K14E | 2 | 5,000-10,000 | 8/10 |
|  | 10 | 10,000-50,000 | 10/10 |
| Y64A | 2 | 5,000-10,000 | 6/10 |
|  | 10 | 10,000-50,000 | 10/10 |
| Y92A | 2 | 1,000-5,000 | 2/10 |
|  | 10 | 10,000-50,000 | 10/10 |
| Adjuvant |  | 50-100 | 0/10 |

NOTE.
Mice were given 10 LD$_{50}$ of wild type (WT) SEA challenge followed by potentiating dose of lipopolysaccharide (150 ug/mouse) 3 h later.
*Reciprocal of serum dilution resulting in optical density reading four times above negative controls (wells containing either no SEA or no primary antibody).

EXAMPLE 8

Immune Recognition of SAg Mutants.

Bacterial SAgs induce clonal anergy of specific subsets of T cells in mice. It was possible that the loss of sensitivity to WT SEA among the mice vaccinated with the attenuated mutant forms represented a state of specific non-responsiveness instead of specific immunity. To address this issue, lymphocyte responses to SEA WT were measured with splenic mononuclear cells collected 2 weeks after the third immunization. As expected, lymphocytes from mice that were immunized with WT SEA or control SEA mutant showed little to no proliferation when incubated with the WT SAg. In contrast, lymphocytes obtained from control mice or those immunized with either Y64A or Y92A all responded vigorously to the WT SEA (FIG. 5). The TCRs used by T cells from the SEA-vaccinated mice were then characterized by flow cytometry. T cells from immunized or control mice were incubated with WT SEA in culture for 7 days, followed by a 5 day expansion in IL-2 containing medium. Distinct populations of activated TCR Vβ11 positive cells were observed with T cells from mice immunized with Y92A and Y64A, representing 48% and 40% of T cells, respectively. However, Vβ11 expressing cells obtained from SEA WT or K14E immunized mice were about 1% and 6% of the total T-cell population, respectively, suggesting that this subset was nonresponsive to restimulation with the WT SAg. T cells bearing Vβ 17a, 3, 7, and 10b were unchanged for all mice. It was apparent that T-cell responses, to both the TCR and MHC class II binding-attenuated SEA mutants were similar to each other, but differed from responses to control or WT molecules. These results suggested that an alternative, perhaps conventional antigen processing mechanism was functioning in presentation of the SAg mutants Y64A and Y92A.

EXAMPLE 9

Rhesus Monkey Immunizations with Monovalent Vaccines.

The SEA vaccine L48R, Y89A, D70R (A489270 and SEB vaccine Y89A, Y94A, L45R (B899445) were used to immunize rhesus monkeys. The animals received a total of three i.m. injections (10-20 μg/animal), given at monthly intervals. Rhesus monkeys that were injected with these vaccines had no detectable increase of serum cytokines and no apparent toxicity. The serological response of animals vaccinated with three doses of formalin-treated SEB toxoid (100 μg/injection) gave results comparable to one or two injections with B899445 (Table 7), suggesting that the recombinant vaccines were very immunogenic. Immunized rhesus monkeys survived a lethal challenge with >10 LD50 of wild-type SEB (Table 7, 8). Collectively, these results suggest that the engineered SEB vaccine is safe, highly antigenic and effective at protecting the immunized individual from lethal aerosol exposure to SEB.

TABLE 7

Rhesus monkey antibody responses to vaccine B899445; One injection of B899445 outperforms three injections of SEB toxoid

| Vaccine[1]/animal # | Antibody response[2] | % Inhibition of T-cell response[3] | Survival SEB >20 × LD50 challenge[4] |
|---|---|---|---|
| preimmune sera/pooled | 0.161 | 5 | dead |
| toxoid/1 | 0.839 | 0 | dead |
| toxoid/2 | 0.893 | 34 | live |
| toxoid/3 | 1.308 | 57 | live |
| toxoid/4 | 1.447 | 55 | live |
| B899445/1 | 1.788 | 69 | live |
| B899445/2 | 0.78 | 49 | live |

[1]Rhesus monkeys were immunized with one dose (20 μg injection) of B899445 vaccine or three doses of formalin-treated SEB toxoid (100 μg/injection) one month apart; both used Alum adjuvants.
[2]Sera were collected one month after the final injection. Antibody responses were determined by ELISA and the results are shown as mean optical densities of triplicate wells (±SEM).
[3]Rhesus monkey T cells, obtained from an untreated animal, were preincubated with diluted (1:70) serum from immunized monkeys and then cultured with wild type SEB. Data are shown as % of Tcell responses, where serum of rhesus monkey injected with adjuvant only represented the 100% of response to wild type SEB.
[4]Rhesus monkeys were challenged by aerosol exposure and monitered for four days.

TABLE 8

Engineered staphylococcal enterotoxin B vaccine efficacy in rhesus monkeys

| Treatment[1] | Antibody titer[2] | Immune protection[3] |
|---|---|---|
| Vaccine with adjuvant | >10,000 | 100% |
| Adjuvant only | <50 | 0% |

[1]Rhesus monkeys (n = 10) were injected i.m. with 10 μg of SEB vaccine with Alhydrogel adjuvant. A total of 3 immunizations, 1 month apart were given. Controls (n = 2) received only Alhydrogel.
[2]Serum dilution resulting in optical density readings of four times above the negative control, consisting of no SEB or serum added to the wells.
[3]Immunized and control rhesus monkeys were challenged with >10 LD50 of wild-type staphylococcal enterotoxin B as an aerosol.

Serum from monkeys that were immunized with the genetically attenuated vaccine inhibited T-lymphocyte responses to wild type SEB (Table 7) similarly or better than monkeys that received the SEB toxoid. Collectively, these results suggest that the recombinant SAg vaccines are safe, highly antigenic, and induce protective immunity.

Serum from B899445 immunized rhesus monkeys blocked human lymphocyte responses to wild-type superantigen when tested in ex vivo cultures (Table 7). These data again showed that the second and third injections of vaccine were approximately equivalent in stimulating neutralizing antibody responses. Normal T-cell responses to several superantigens, including the wild-type protein, were observed in immunized animals, indicating that no specific or generalized anergy occurred (FIG. 6).

EXAMPLE 10

A. Multivalent Superantigen Vaccines: Rhesus Monkey Immunizations.

Rhesus monkeys were immunized with a combined vaccine consisting of B899445 and A489270. Following the third injection, antibody recognition of wild-type bacterial superantigens was examined (FIG. 7). High titers of anti-SEB, SEC1 and SEA antibodies were evident.

B. Mouse Immunizations.

Mice (BALB/c) were immunized with a combined vaccine consisting of SEA, SEB, SEC1 and TSST-1 (all wild-type). The antibody responses against each individual superantigen were assessed (Table 9). Antibodies were induced against each of the component antigens, providing sufficient levels to protect the mice from a lethal challenge of superantigen, potentiated with LPS. Although not shown in the Table, antibody responses against SPE-A were also observed. Mice were also immunized with individual superantigens and antibody responses against other superantigens were measured (Table 10). Each individual immunogen induced partial or complete protective antibody responses against all other superantigens tested.

TABLE 9

Superantigen cross-reactivity of antibodies from mice immunized with individual bacterial superantigens

| Immunizing[1] Toxin | Challenging[2] Toxin | ELISA[3] Titer | Neutralizing[4] Antibody |
|---|---|---|---|
| SEA | SEA | >1/25,000 | 100% |
| SEA | SEB | >1/25,000 | 100% |
| SEA | SEC1 | >1/25,000 | 100% |
| SEA | TSST1 | >1/10,000 | 100% |
| SEB | SEB | >1/25,000 | 100% |
| SEB | SEA | >1/10,000 | 100% |
| SEB | SEC1 | >1/2,500 | 100% |
| SEB | TSST1 | >1/10,000 | 100% |
| SEC1 | SEC1 | >1/10,000 | 100% |
| SEC1 | SEA | >1/10,000 | 100% |
| SEC1 | SEB | >1/25,000 | 100% |
| SEC1 | TSST1 | >1/10,000 | 100% |
| TSST1 | TSST1 | <1/10,000 | 100% |
| TSST1 | SEA | <1/1,000 | 50% |
| TSST1 | SEB | <1/1,000 | 40% |
| TSST1 | SEC1 | <1/1,000 | 40% |

[1]Three injections with 20 ug of antigen (BALB/c mice).
[2]LPS-potentiated challenge with 10 $LD_{50}$s of superantigen.
[3]ELISA antibody response against an individual superantigen.
[4]Percent mice surviving an LPS-potentiated challenge (n = 10).

TABLE 10

Multivalent superantigen vaccine. Mouse immune responses.

| Immunizing toxin[1] | Challenging toxin[2] | Antibody Titer[3] | % survival |
|---|---|---|---|
| SE-A, B, C1, TSST-1 | all | N/A | 100% |
| " | SEA | >25,000 | 100% |
| " | SEB | >25,000 | 100% |
| " | SEC1 | >25,000 | 100% |
| " | TSST-1 | >6,400 | 100% |

[1]Total of three injections, two weeks apart, in RIBI adjuvant.
[2]>10 × LD50, potentiated with *E. coli* lipopolysaccharide.
[3]Measured by ELISA.

EXAMPLE 11

Design of Altered TSST-1 Toxin Vaccine, TST30.

A comprehensive study of the relationships of TSST-1 protein structure to receptor binding were undertaken to provide insight into the design of the vaccine TST30. We have discovered that TSST-1 interactions with the human MHC class II receptor, HLA-DR, are relatively weak and can be disrupted by altering only a single critical amino acid residue of the toxin. Site-directed mutagenesis of a gene encoding the toxin and expression of the new protein product in *E. coli* were then used to test the design of the vaccine. The TSST-1 gene used was contained within a fragment of DNA isolated by BglI restriction enzyme digestion of the gene isolated from a toxigenic strain of *Staphylococcus aureus* (AB259; Kreiswirth and Novick (1987) *Mol. Gen. Genet.* 208, 84-87). The sequence of this gene is identical to all currently known TSST-1 isolates of human origin. The wild-type TSST-1 gene can be readily cloned from a number of clinical *S. aureus* isolates. The DNA fragment containing the TSST-1 gene was isolated by agarose gel electrophoresis and ligated inot the prokaryotic expression vector pSE380 (Invitrogen Corp.). The DNA clone consisted of sequences encoding the leader peptide and the full length of the mature TSST-1 protein. This engineered vaccine is currently being evaluated to determine mouse and human T-cell reactivities in vitro, and lethality in mice. The TST30 vaccine consists of the following mutation introduced into the toxin molecule: leucine at amino acid residue 30 changed to arginine. Two other mutations, namely Asp27 to Ala and Ile46 to Ala have also been designed. The final vaccine may incorporate one or both of these additional mutations.

The binding interface between TSST-1 and HLA-DR consists of a large relatively flat surface located in the N-terminal domain. Leucine 30 protrudes from a reverse turn on the surface of TSST-1 and forms the major hydrophobic contact with the HLA-DR receptor molecule. Mutation of the single residue leucine 30 in TSST-1 to the charged amino acid side chain of arginine is predicted to disrupt this major contact with the receptor molecule, resulting in a significant reduction in DR1 binding. This mutant molecule should therefore have lost the toxin attributes of the wild-type molecule.

TST30 was expressed as a recombinant protein in *E. coli*, as either a periplasmically secreted protein or as a cytoplasmic product. Purification was achieved by immunoaffinity chromatography or preparative isoelectric focusing after an initial ion-exchange CM-Sepharose enrichment step. The method of purification was not critical to the performance of the vaccine. Lipopolysaccharide contaminants, resulting from expression in a Gram-negative bacterium, were readily removed (as determined by limulus assay) using a variety of standard methods. The final purified vaccine is not toxic to mice at levels equivalent to 10 $LD_{50}$ of the native TSST-1. No indicators of toxicity were found in surrogate assays of human T-cell stimulation.

Conclusive vaccine studies demonstrating that TST30 is highly antigenic and induces protective immunity are in progress in a mouse animal model. Mouse lethality is achieved at less than 1 ug/animal when a potentiating signal like lipopolysaccharide from Gram-negative bacteria (LPS) is provided. When coadministered with LPS, wild-type TSST-1 is 100% lethal to mice (10 $LD_{50}$). Mice receive three injections (two weeks between injections) of 20 ug/mouse in alhydrogel and protection against the lethal effects of 10 $LD_{50}$ of TSST-1 are assessed.

EXAMPLE 12

Design of Altered SPEA Toxin Vaccine, SPEa42

The SPEa interactions with human MHC class II receptor, HLA-DR, are relatively weak and can be disrupted by altering only a single critical amino acid residue of the toxin. Site-directed mutagenesis of a gene encoding the toxin and expression of the new protein product in *E. coli* were then used to test the design of the vaccine. The SPEa gene used was clone from a SPEa-toxigenic strain of *Streptococcus* by using specific DNA oligonucleotide primers and the polymerase chain reaction method. The sequence of this gene is identicla to SPEa isolates of human origin known within the public domain. The DNA fragment containing the SPEa gene was isolated by agarose gel electrophoresis and ligated into a prokaryotic expression vector (pETx or pSE380). The DNA clone consisted of sequences encoding the leader peptide and the full length of the mature SPEa protein or SPEa42 without a leader sequence. We recognize that there are additional ways to express or produce the mature SPEa vaccine. The SPEa vaccine consists of the following mutation introduced into the toxin molecule: leucine at amino acid residue 42 changed to arginine.

The binding interface between SPEa and HLA-DR is predicted to consist of contacts located in the N-terminal domain that are conserved with other bacterial superantigens. Leucine 42 of SPEa is predicted to protrude from a reverse turn on the surface of SPEa and form a major hydrophobic contact with the HLA-DR receptor molecule. Mutation of the single residue leucine 42 in SPEa to the charged amino acid side chain of arginine is predicted to disrupt this major contact with the receptor molecule, resulting in a significant reduction in DR1 binding. This mutant molecule should therefore have lost the toxin attributes of the wild-type molecule.

SPEa42 was expressed as a recombinant protein in *E. coli*, as either a periplasmically secreted protein or as a cytoplasmic product. Purification was achieved by immunoaffinity chromatography or preparative isoelectric focusing after an initial ion-exchange CM-Sepharose enrichment step. The method of purification was not critical to the performance of the vaccine. Lipopolysaccharide contaminants, resulting from expression in a Gram-negative bacterium, were readily removed (as determined by limulus assay) using a variety of standard methods. The final purified vaccine is not toxic to mice at levels equivalent to 10 $LD_{50}$ of the native TSST-1. No indicators of toxicity were found in surrogate assays of human T-cell stimulation.

Conclusive vaccine studies demonstrating that SPEa42 is highly antigenic and induces protective immunity are in progress in a mouse animal model. Mouse lethality is achieved at less than 1 ug/animal when a potentiating signal like lipopolysaccharide from Gram-negative bacteria (LPS) is provided. When coadministered with LPS, wild-type SPEa is 100% lethal to mice (10 $LD_{50}$). Mice receive three injections (two weeks between injections) of 20 ug/mouse in alhydrogel and protection against the lethal effects of 10 $LD_{50}$ of SPEa are assessed

EXAMPLE 13

Design of Altered Superantigen Toxin Vaccine, SEC45

For Staphylococcal enterotoxin C1 (SEC1), the leucine at position 45 was changed to lysine (SEC45). This mutation is anticipated to prevent SEC1 from interacting with the MHC class II receptor by sterically blocking the hydrophobic loop (centered around leucine 45) from binding to the alpha chain of the receptor. SEC1 is more closely homologous to SEB than SEA or the other superantigen toxins. The presence of zinc in SEC1 may impart additional binding characteristics that allow, in some cases, this superantigen toxin to bind to T-cell antigen receptors without the required MHC class II molecule interactions. To circumvent the binding to T-cell antigen receptors, mutations of SEC1 residues N23 (changed to alanine), V91 (changed to lysine) are being performed.

What is claimed is:

1. An isolated and purified superantigen toxin DNA fragment encoding Staphylococcal enterotoxin B (SEB) in which one amino acid located within positions 40-50, and at least one amino acid located within amino acid positions 55-65, 62-72, 84-94, 86-96, 89-99, 110-120 and 205-215 has been altered such that binding of said encoded SEB to the MHC class II receptor and T cell antigen receptor is altered.

2. A recombinant DNA construct comprising:
   (i) a vector, and
   (ii) an isolated and purified altered superantigen toxin DNA fragment according to claim 1.

3. An isolated host cell transformed with the recombinant DNA construct according to claim 2.

4. A host cell according to claim 3, wherein said cell is prokaryotic.

5. A method for producing altered superantigen toxin comprising culturing the cells according to claim 3, under conditions such that said DNA fragment is expressed and said superantigen toxin is thereby produced, and isolating said superantigen toxin.

6. The superantigen toxin DNA fragment according to claim 1, wherein an amino acid is altered within the range of amino acids located at positions 18-28.

7. The superantigen toxin DNA fragment according to claim 1, wherein an amino acid is altered within the range of amino acids located at positions 55-65.

8. The superantigen toxin DNA fragment according to claim 1, wherein an amino acid is altered within the range of amino acids located at positions 62-72.

9. The superantigen toxin DNA fragment according to claim 1, wherein an amino acid is altered within the range of amino acids located at positions 84-94.

10. The superantigen toxin DNA fragment according to claim 1, wherein an amino acid is altered within the range of amino acids located at positions 86-96.

11. The superantigen toxin DNA fragment according to claim 1, wherein an amino acid is altered within the range of amino acids located at positions 89-99.

12. The superantigen toxin DNA fragment according to claim 1, wherein an amino acid is altered within the range of amino acids located at positions 110-120.

13. The superantigen toxin DNA fragment according to claim 1, wherein an amino acid is altered within the range of amino acids located at positions 205-215.

* * * * *